(12) United States Patent
Davidson et al.

(10) Patent No.: US 10,391,184 B2
(45) Date of Patent: Aug. 27, 2019

(54) METHODS AND COMPOSITIONS FOR TREATING BRAIN DISEASES

(71) Applicants: UNIVERSITY OF IOWA RESEARCH FOUNDATION, Iowa City, IA (US); Luis Tecedor, Iowa City, IA (US); Yong Hong Chen, Iowa City, IA (US)

(72) Inventors: Beverly L. Davidson, Iowa City, IA (US); Luis Tecedor, Iowa City, IA (US); Yong Hong Chen, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 14/907,776

(22) PCT Filed: Jul. 20, 2014

(86) PCT No.: PCT/US2014/047338
§ 371 (c)(1),
(2) Date: Jan. 26, 2016

(87) PCT Pub. No.: WO2015/013148
PCT Pub. Date: Jan. 29, 2015

(65) Prior Publication Data
US 2016/0166709 A1    Jun. 16, 2016

Related U.S. Application Data
(60) Provisional application No. 61/859,157, filed on Jul. 26, 2013.

(51) Int. Cl.
*A61K 48/00* (2006.01)
*A61K 31/343* (2006.01)

(52) U.S. Cl.
CPC ........ *A61K 48/0058* (2013.01); *A61K 31/343* (2013.01); *A61K 48/0075* (2013.01); *A61K 48/00* (2013.01); *C12N 2750/14143* (2013.01)

(58) Field of Classification Search
CPC .................. A61K 48/0058; A61K 48/0075
See application file for complete search history.

(56) References Cited

U.S. PATENT DOCUMENTS

| | | | |
|---|---|---|---|
| 2002/0049178 A1 | 4/2002 | Goldman et al. | |
| 2013/0158104 A1 | 6/2013 | Lopez et al. | |
| 2013/0195801 A1* | 8/2013 | Gao | C12N 15/86 424/93.2 |

FOREIGN PATENT DOCUMENTS

| | | |
|---|---|---|
| RU | 2008152821 A | 7/2010 |
| WO | 2006060641 A2 | 6/2006 |
| WO | 2012135857 A1 | 10/2014 |

OTHER PUBLICATIONS

Carson et al. Immunol. Rev. 213-48-65, 2006; printout cited as pp. 1-27.*
Castellano, et al., "Human apoE isoforms differentially regulate brain amyloid-β peptide clearance", Sci Transl Med. 3 (89), 89ra57 (2011).
Chang, et al., "Intraventricular Enzyme Replacement Improves Disease Phenotypes in a Mouse Model of Late Infantile Neuronal Ceroid Lipofuscinosis", Molecular Therapy 16, 649-656, (2008).
Fu, et al., "Restoration of central nervous system alpha-N-acetylglucosaminidase activity and therapeutic benefits in mucopolysaccharidosis IIIB mice by a single intracisternal recombinant adeno-associated viral type 2 vector delivery", J Gene Med 12, 624-633 (2010).
Fu, et al., "Significantly increased lifespan and improved behavioral performances by rAAV gene delivery in adult mucopolysaccharidosis IIIB mice", Gene Therapy 14, 1065-1077 (2007).
Patent Cooperation Treaty, "International Searching Authority, Search Report and Written Opinion for PCT/US2014/047338, 11 pages, dated Nov. 13, 2014."
Sands, et al., "Gene therapy for lysosomal storage diseases", Mol Ther 13 (5), 839-849 (2006).
Chakrabarty, et al., "Hippocampal Expression of Murine IL-4 results in Exacerbation of Amyloid Deposition", Molecular Neurodegeneration, vol. 7, No. 36 p. 1-12 (2012).
Gray, et al., "Global CNS Gene Delivery and Evasion of Anti-AAV Neutralizing Antibodies by Intrathecal AAV Administration in Non-Human Primates", Gene Ther. vol. 20, No. 4, 450-459 (2013).
Haurigot, et al., "Toward a Gene Therapy for Neurological and Somatic MPSIIIA", Rare Diseases, vol. 1, No. 1, e. 27209 (2013).
Katz, et al., "AAV Gene Transfer Delays Disease Onset in a TPPI-deficient Canine Model of the Late Infantile Form of Batten Disease", www.ScienceTranslationalMedicine.org, Research Article, Gene Therapy, vol. 7, Issue 313, (2015).
Shin, et al., "A Simplified Immune Suppression Scheme Leads to Persistent Micro-Dystrophin Expression in Duchenne Muscular Dystrophy Dogs", Human Gene Therapy, vol. 23, 202-209 (2012).
Worgall, et al., "Treatment of Late Infantile Neuronal Ceroid Lipofuscinosis by CNS Administration of a Serotype 2 Adeno-Associated Virus Expressing CLN2 cDNA", Human Gene Therapy, vol. 19, 1-23 (2008).

(Continued)

*Primary Examiner* — Marcia S Noble
(74) *Attorney, Agent, or Firm* — Viksnins Harris Padys Malen LLP

(57) ABSTRACT

The present disclosure provides methods of treating a disease or delivering a therapeutic agent to a mammal comprising administering to the mammal's cisterna magna and/or ventricle an rAAV particle containing a vector comprising a nucleic acid encoding a therapeutic protein inserted between a pair of AAV inverted terminal repeats in a manner such that cells with access to the cerebrospinal fluid (CSF) express the therapeutic agent and in certain embodiments secretes the therapeutic agent into the CSF for distribution to the brain.

20 Claims, 29 Drawing Sheets
Specification includes a Sequence Listing.

(56) References Cited

OTHER PUBLICATIONS

Feng, et al., "Adeno-associated viral vector-mediated ApoE expression in Alzheimer's disease mice: low CNS immune response, long-term expression, and astrocyte specificity", Front Biosci 9, 1540-1546 (2004).

Ozawa, "Gene therapy using AAV", Virus 57(1), 1540-1546 (2004). [English Abstract included.]

Mizuguchi, "Recent Advances in Adenovirus Vectors—Focusing on development of improved vectors aimed at suppressing immune responses-", Protein, Nucleic Acid and Enzyme vol. 44 No. 9, 1405-1446 (1999).

* cited by examiner

Figure 1A-1

ClustalW (v1.83) multiple sequence alignment

2 Sequences Aligned          Alignment Score = nan
Gaps Inserted = 7            Conserved Identities = 446

Pairwise Alignment Mode: Slow
Pairwise Alignment Parameters:
  Open Gap Penalty = 10.0    Extend Gap Penalty = 0.1
  Similarity Matrix: gonnet Multiple Alignment Parameters:
  Open Gap Penalty = 10.0    Extend Gap Penalty = 0.1
  Delay Divergent = 40%      Gap Distance = 8
  Similarity Matrix: gonnet Processing time: 0.2 seconds AAV4capPro    1 -MTDGYLPDWLEDNLSEGVREWWALQPGAPKPKANQQHQDNARGLVLPGYKYLGPGNGLD  59
AAV2capPro    1 MAADGYLPDWLEDTLSEGIRQWWKLKPGPPPPKPAERHKDDSRGLVLPGYKYLGPFNGLD  60
                 ***************** *** *.** * ** ..*.* .*************** **

AAV4capPro   60 KGEPVNAADAAALEHDKAYDQQLKAGDNPYLKYNHADAEFQQRLQGDTSFGGNLGRAVFQ 119
AAV2capPro   61 KGEPVNEADAAALEHDKAYDRQLDSGDNPYLKYNHADAEFQERLKEDTSFGGNLGRAVFQ 120
                ****** *.**********  .*******************. .*******************

AAV4capPro  120 AKKRVLEPLGLVEQAGETAPGKKRPLIESPQQPDSSTGIGKKGKQPAKKKLVFEDETGAG 179
AAV2capPro  121 AKKRVLEPLGLVEEPVKTAPGKKRPVEHSPVEPDSSSGTGKAGQQPARKRLNFGQTGDAD 180
                ***********  *****  .****.* ** *.****.*.. * *

Figure 1A-2

```
AAV4capPro  180 DGP---PEGSTSGAMS--DDSEMRAAAGGAAVEGGQGADGVGNASGDWHCDSTWSEGHVT 234
AAV2capPro  181 SVPDPQPLGQPPAAPSGLGTNTMATGSGAPMADNNEGADGVGNSSGNWHCDSTWMGDRVI 240
                 **  *   *    **      *  *  .  *              ***.** ********. *

AAV4capPro  235 TTSTRTWVLPTYNNHLYKRLG---ESLQSNTYNGFSTPWGYFDFNRFHCHFSPRDWQRLI 291
AAV2capPro  241 TTSTRTWALPTYNNHLYKQISSQSGASNDNHYFGYSTPWGYFDFNRFHCHFSPRDWQRLI 300
                ******* ********* :      . * *.*.  ************************

AAV4capPro  292 NNNWGMRPKAMRVKIFNIQVKEVTTSNGETTVANNLTSTVQIFADSSYELPYVMDAGQEG 351
AAV2capPro  301 NNNWGFRPKRLNFKLFNIQVKEVTQNDGTTTIANNLTSTVQVFTDSEYQLPYVLGSAHQG 360
                ***** ***   . :********.. *:*. ********:*:**.*:****: .:*:*

AAV4capPro  352 SLPPFPNDVFMVPQYGYCGLVTGNTSQQQTDRNAFYCLEYFPSQMLRTGNNFEITYSFEK 411
AAV2capPro  361 CLPPFPADVFMVPQYGYLTLNNG---SQAVGRSSFYCLEYFPSQMLRTGNNFTFSYTFED 417
                .****.***********  . .*    **..  : **************** : ** *

AAV4capPro  412 VPFHSMYAHSQSLDRLMNPLIDQYLWGLQSTTTGTTLNAGTATTNFTKLRPTNFSNFKKN 471
AAV2capPro  418 VPFHSSYAHSQSLDRLMNPLIDQYLYYLSRTNTPSGTTT-QSRLQFSQAGASDIRDQSRN 476
                *****  ****************   *..*.*  ****   .::*:            *

AAV4capPro  472 WLPGPSIKQQGFSKTANQNYKIPATGSDSLIKYETHSTLDGRWSALTPGPPMATAGPADS 531
AAV2capPro  477 WLPGPCYRQQRVSKTSADNNNSEYSWTG----ATKYHLNGRDSLVNPGPAMASHKDDEE 531
                ***** . ** .***:*:*:**:*.*      ** **   * :****:**: .: 
```

Figure 1A-3

```
AAV4capPro  532 KFS-NSQLIFAGPKQNGNTATVPGTLIFTSEEELAATNATDTDMWGNLPGGDQSNSNLPT 590
AAV2capPro  532 KFFPQSGVLIFGKQGSEKTNVDIEKVMITDEEEIRTTNPVATEQYGSVSTNLQRGNRQAA 591
                 **  *  * *** .*** ..  .. * *** .**  **  .  * *  .   *  .

AAV4capPro  591 VDRLTALGAVPGMVWQNRDIYYQGPIWAKIPHTDGHFHPSPLIGGFGLKHPPPQIFIKNT 650
AAV2capPro  592 TADVNTQGVLPGMVWQDRDVYLQGPIWAKIPHTDGHFHPSPLMGGFGLKHPPPQILIKNT 651
                 .. * .******  **.* .************************:************

AAV4capPro  651 PVPANPATTFSSTPVNSFITQYSTGQVSVQIDWEIQKERSKRWNPEVQFTSNYGQQNSLL 710
AAV2capPro  652 PVPANPSTTFSAAKFASFITQYSTGQVSVEIEWELQKENSKRWNPEIQYTSNYNKSVNVD 711
                ******.***** .  *.************ *:**:*:**:*****:*:*****..  .

AAV4capPro  711 WAPDAAGKYTEPRAIGTRYLTHHL 734
AAV2capPro  712 FTVDTNGVYSEPRPIGTRYLTRNL 735
                 *. *   * **** ******..*
```

Figure 1B-1

ClustalW (v1.83) multiple sequence alignment

2 Sequences Aligned          Alignment Score = nan
Gaps Inserted = 10           Conserved Identities = 1440

Pairwise Alignment Mode: Slow
Pairwise Alignment Parameters:
  Open Gap Penalty = 10.0    Extend Gap Penalty = 5.0

Multiple Alignment Parameters:
  Open Gap Penalty = 30.0    Extend Gap Penalty = 5.0
  Delay Divergent = 40%      Transitions: Weighted Processing time: 1.8 seconds 1. AAV2capNuc vs. AAV4capNuc1

Aligned Length = 2235    Gaps = 10
Identities = 1440 (65%)

```
AAV2capNuc   1 ATGGCTGCCGATGGTTATCTTCCAGATTGGCTCGAGGACACTCTCTGAAGGAATAAGA   60
AAV4capNuc1  1 ---ATGACTGACGGTTACCTTCCAGATTGGCTGGCTAGAGGACAACCTCTTCGAAGGCGTTCGA   57
               * ** ********** ******************** * **

AAV2capNuc  61 CAGTGGTGGAAGCTCAAACCTGGCCCACCACCAAAGCCCGCAGAGCGGCATAAGGAC  120
AAV4capNuc1 58 GAGTGGTGGGGCGCTGCAACCTGGAGCCCTAAACCCAAGGCAAATCAACACATCAGGAC  117
               ******** ** * *** *** * * *** *****
```

Figure 1B-2

```
AAV2capNuc   1121 GACAGCAGGGGTCTTTGTGCTTCCTGGGTACAAGTACCTCGGACCCCTTCAACGGACTCGAC 180
AAV4capNucl  1118 AACGCTCGGGGTCTTTGTGCTTCCGGGTTACAAATACCTCGGACCCGGACAACGGACTCGAC 177
                   **  ***  *************** ***** ******** *****************

AAV2capNuc   181 AAGGGAGAGCCGGTCAACGAGGCAGACGCGCGGCCCTCGAGCACGACAAAGCCTACGAC 240
AAV4capNucl  178 AAGGGGGAACCCGTCAACGTCAACGCAGCGGACGGGCAGCCCTCGAGCACGACAAGGCCTACGAC 237
                 ***** **  ** ***** **   ** * *** ********* *********** ******

AAV2capNuc   241 CGGCAGCTCGACAGCGGGGAGACAACCCGTACCTCAAGTACAACCACGCCGACGCGGAGTTT 300
AAV4capNucl  238 CAGCAGCTCAAGGCCGGTGACAACCCGTACCTCAAGTACAACCACGCCGACGCGGAGTTC 297
                 * ******* *    ** ***  **************************** *********

AAV2capNuc   301 CAGGAGCGCCTTAAAGAAGATACGTCTTTTGGGGCAACCTCGGACGAGCAGTCTTCCAG 360
AAV4capNucl  298 CAGCAGCGGCTTCAGGGCGACACATCGTTTGGGGGCAACCTCGGCAGAGCAGTCTTCCAG 357
                 *** ***  ***  *  ** ** ** *** **** *********  ***************

AAV2capNuc   361 GCGAAAAAGAGGGTTCTTGAACCTCTGGGCCTCGGTTGAGGAACCTGTTAAGACGGCTCCG 420
AAV4capNucl  358 GCCAAAAAGAGGGTTCTTGAACCTCTGGTCTCGGTTGAGCAAGCGGGGTGAGACGGCTCCT 417
                 ** **********************  ** ********* **   * * *******  **

AAV2capNuc   421 GGAAAAAAGAGGCCGGTAGAGCCACTCTCCTGTGAGCCAGACTCCTCCTCGGAACCGGA 480
AAV4capNucl  418 GGAAAGAAGAGACCGTTGATTGAATCCCCCAGCAGCCCGACTCCTCCTCCACGGGTATCGC 477
                 *****  ****  ** * ***  *   *  ** *****  ************ **  ***

AAV2capNuc   481 AAGGCGGGCCAGCAGCCTGCAGAAGAAAAAGATTGAATTTGGTCAGACTGGAGACGCAGAC 540
AAV4capNucl  478 AAAAAAGGCAAGCAGCAGCCGGCTAAAAAGAAGAAGCTCGTTTTTCGA------AGACGAAACT 528
                 **  *** **  *  **  * **      **   *  *    ***  *    ***** *
```

Figure 1B-3

```
AAV2capNuc   541 TCAGTACCTGACCCCCAGCCTCTCGGACAGCAGCCACCAGCAGCCCCCTCTGGTCTGGAACT 600
AAV4capNucl  529 GGAGCAGGCGACGGACCCCCTGAGGGATCAACTTCCGGAGCCATGTCTGAT-----GAC   582
                  ** *    ***   *  **** * * ****  ****    *

AAV2capNuc   601 AATACGGATGGCTACAGGCAGTGGCGCACCAATGGCAGACAATAACGAGGGCGCCGACGGA 660
AAV4capNucl  583 AGTGAGATGCGTGCAGCAGCTGCGGGAGCTGCAGTGCAGTCGAGGGCGGACAAGGTGCCGATGGA 642
                 * * ****  *  **  ***  **     ** * ** ** *   * ** ***** *** ***

AAV2capNuc   661 GTGGGTAATTCCTCGGGAAATTGGCATTGCGATTCCACATGGATGGGCGACAGAGTCATC 720
AAV4capNucl  643 GTGGGTAATGCCCTCGGGTGATTGGCATTGCGATTCCACCTGGTCTGAGGGCCACGTCACG 702
                 ********* ** ****** *************** ***  *** *  ** ** ****

AAV2capNuc   721 ACCACCAGCACCCGAACCTGGGCCCCTGCCCACCTACAACAACCACCTCTACAAACAAATT 780
AAV4capNucl  703 ACCACCAGCACCAGAACCTGGGTCTTGCCCACTGGGTCTTGCCCACTGCCACCTCTACAAGCAGGACTC 762
                 ************ ********  *  *****   *   * ****   ** ************  * *

AAV2capNuc   781 TCCAGCCAATCAGGAGCCTCGAACGACAATCACTACTTTGGCTACAGCACCCCTTGGGGG 840
AAV4capNucl  763 GG-------AGAGAGCCTGCAGTCCAGTGCAGCCCTGCCAACAACGGATTCTCCACCCCCTGGGGA 813
                  *       ** ****     ***  *   *** *  ** ****  *  ** ****** *****

AAV2capNuc   841 TATTTTGACTTCAACAGATTCCACTGCCACTTTTCACCACGTGACTGGCAAAGACTCATC 900
AAV4capNucl  814 TACTTTGACTTCAACCGCTTCCACTGCCACTTCTCCACCACGTGACTGGCAGCGACTCATC 873
                 ** ************ *  ***********   * * ****************  ********

AAV2capNuc   901 AACAACAACTGGGGATTCCGACCCAAGAGACTCAACTTCAAGCTCTTTAACATTCAAGTC 960
AAV4capNucl  874 AACAACAACTGGGCATGCCGACCCAAAGCCATGCCATGCGGGTCAAAATCTTCAACATCCAGGTC 933
                 *************  * ******** *     * ****  ****** ***** ***
```

Figure 1B-4

```
AAV2capNuc   961 AAAGAGGTCACGGCAGAATGACGAGTACGACGGTATGCCAATAACCTTACCAGCACGGTT 1020
AAV4capNuc1  934 AAGGAGGTCACGACGACGTCGAACGGCGAGACAACGGTGGCTAATAACCTTACCAGCACGGTT 993
                 ** **********   *         *** *  **  **********************

AAV2capNuc  1021 CAGGTGTTTACTGACTCGGAGTACCAGCTCCCGTACGTCCTCGGCTCGGGCATCAAGGA 1080
AAV4capNuc1  994 CAGATCTTTGCGGACTCGTCGTACGAACTGCCGTACGTGATGGATGCGGGTCAAGAGGGC 1053
                 *** * *** * ****** * ***** ** *** ***  *    *** *  **    **

AAV2capNuc  1081 TGCCTCCCGCCGTTCCCAGCAGAGACGTCTTCATGGTGCCACAGTATGGATACCTCACCCTG 1140
AAV4capNuc1 1054 AGCCTGCCTCCTTTTCCCAACGACGTCTTTATGGTGCCCCAGTACGGCTACTGTGGACTG 1113
                 *** ** ** ** **** ** ********* *******  **** ** **  ** ** *

AAV2capNuc  1141 AACAACGGGAGT--CAGGCAGTAGGACGCTC------TTCATTTTACTGCCTGGAGTAC 1191
AAV4capNuc1 1114 GTGACCGGCAACACTTCGCAGCAACACTTCGCAGCAACAGAAATGCCTTCTACTGCCTGGAGTAC 1173
                   *  ***  *      **    *     *                * **************

AAV2capNuc  1192 TTTCCTTTCTCAGATGCTGCGTACCGGAAACAACTTTACCTTCAGCTACACTTTGAGGAC 1251
AAV4capNuc1 1174 TTTCCTTCGCAGATGCTGCGTGGGACTGGCAACAACTTTGAAATTACGTACAGTTTGAGAAG 1233
                 ******* ***********  *  * ** ********  * ****  *** ********

AAV2capNuc  1252 GTTCCTTTCCACAGCAGCTACGCTCCACAGCCAGAGTCTGGACCGTCTCATGAATCCTC 1311
AAV4capNuc1 1234 GTGCCTTTTCCACTCACTCGATGTACGGCGCAGCAGAGCCTGGACCGGACCGGCTGATGAACCCCTC 1293
                   * *****   *     * *    * *   ** **** ********  ** *** * *******

AAV2capNuc  1312 ATCGACCAGTACCTGTATTACTTGAGCAGAACAAACACTCCAAGTGGAACCACCAGCAG 1371
AAV4capNuc1 1294 ATCGACCAGTACCTGTGGGGACTGCAATGACCACCACCACCGGAACCACCCCTGAATGCCGGGG 1353
                 ****************         **        ***    **  ** *   *
```

Figure 1B-5

```
AAV2capNuc  1372 TCAA--GGCTTCAGTTTTCTCAGGCCGGAGCG-AGTGACATTCGGGACCAGTCTAGGAAC 1428
AAV4capNucl 1354 ACTGCCACCACCAACTTTACCAAGCTGCGGCCTACCAACTTTTCCAACTTTAAAAAGAAC 1413
                  *       *  **   *  **    ***   *   **  **   *   *  * ****

AAV2capNuc  1429 TGGCTTCCTGGACCCTGTTACCGGCAGCAGGAGTATCAAAGACATCTGCGGATAACAAC 1488
AAV4capNucl 1414 TGGCTGCCCCGGGCCCTTCAATCAAGCAGCAGCAGGGCTTCTCAAAGACTGCCAATCAAAACTAC 1473
                 **** * **  *  ** **  *   ** **  **  ***  * *    * ****** *

AAV2capNuc  1489 AACAG---TGAATACTCGTGGACTGGAGCTACCAAGTACCA-------CCTCAAT 1533
AAV4capNucl 1474 AAGATCCCTGCCACCGGGTCAGACAGTCTCATCAAATACGAGACGCACAGCACTCTGGAC 1533
                 **  *       **  **  *   **  *   *  *  *** ***  *       **  *

AAV2capNuc  1534 GGCAGAGACTCTCTGGTGAATCCGGGCCCGGCCCATGGCAAGCCACAAGGACCACAAGGCGATGAAGAA 1593
AAV4capNucl 1534 GGAAGATGGAGTGCCCTGACCCCCCGACCTCCAATGGCCACGGTCCACGGGCTGGACCTGCGGACAGC 1593
                 **  ** *     *     **  *   *  *** ** * *****  *  **

AAV2capNuc  1594 AAGTTTTTCCTCAGAGCGGGGTTTCTCATCTTTGGGAAGCAAGGCTCAGAGAAAACAAAT 1653
AAV4capNucl 1594 AAGTTCAG---CAACAGCCAGCTCAGCTCATCTTTGCGGGGCCTAAACAGAACGGCAACACAGGCC 1650
                 *****         ** *     * ** **** *  **    *  *  ** *  **

AAV2capNuc  1654 GTGGACATTGAAAAGGTCATGATTACAGACGAAGAGGAAATCAGGACAACCAATCCCGTG 1713
AAV4capNucl 1651 ACCGTACCCGGGACTCTGATCTTCACCTGCGGAGGAGCTGGCAGCCAGCCACCAACGCCACC 1710
                  * *    **         **  **   *  **  **  ** **  *  * ******  **

AAV2capNuc  1714 GCTACGGGAGCAGTATGGTTCTGTATCTACCAACCTCCAGAGAGGCAACAGACAAGCAGCT 1773
AAV4capNucl 1711 GATACGGACATGTGGGCAACCTACCTGCCGGTGACCAGAGCAACAGCAACCTGCCGACC 1770
                 * *****        *  **    **       *  *   ***** * * * *   *
```

Figure 1B-6

```
AAV2capNuc  1774 ACCGCAGATGTCAACACACAAGGCGTTCTTCCAGGCATGGTCTGGCAGGACAGAGATGTG 1833
AAV4capNucl 1771 GTGGACAGACTGACAGCCTTGGGAGCCGTGCCTGGAATGGTCTGGCAAAACAGAGACATT 1830
                   *  *    *     *   **  **        *  *********   ****** *

AAV2capNuc  1834 TACCTTCAGGGCCCATCTGGGCAAAGATTCCACACGGACGGACATTTCACCCCTCT 1893
AAV4capNucl 1831 TACTACCAGGGTCCCATTTGGGCAAGATTCCTCATACCGATGGACACTTTCACCCCTCA 1890
                 *** ** ***** ** ***  ********  **  ** ** ***** *********

AAV2capNuc  1894 CCCCTCATGGGTGGATTCGGACTTAAACACCCTCCTCCACAGATTCTCATCAAGAACACC 1953
AAV4capNucl 1891 CGGCTGATTGGTGGGTTTGGGCTGAAACACCCCGCCTCCTCAAATTTTATCAAGAACACC 1950
                 *  ** ** ***** ** ** ** ********  ** ***  ***** ***********

AAV2capNuc  1954 CCGGTACCTGCGAATCCTTCGACCACCTTCAGTGCGGCAAAGTTTGCTTCCTTCATCACA 2013
AAV4capNucl 1951 CCGGTACCTGCGAATCCTGCAACGACCTTCAGCTCTCCGGTAAACTCCTTCATTACT 2010
                 ****************  *  * *********    *** ***  **  ***** ** **

AAV2capNuc  2014 CAGTACTCCACGGGACAGGTCAGCGTCGAGATCGAGTGGGAGCTGCAGAAGGAAAACAGC 2073
AAV4capNucl 2011 CAGTACAGCACTGGCCAGGTGTCCGTCGAGATTGACTGGGAGATTGACTGGAGCCGGTCC 2070
                 ******  ***  * *****  * ********  ** ******    *  *********

AAV2capNuc  2074 AAACGCTGGAATCCCGAAATTCAGTACACTTCCAACTACAACAAGTCTGTTAATGTGGAC 2133
AAV4capNucl 2071 AAACGCTGGAACCCCGAGGTTCAGTTCACCTTACCTCCAACTACGACAGCAAAACTCTGTTG 2130
                 ***********  ****  *****  **  * **  ** **   **         ** ** *

AAV2capNuc  2134 TTTACTGTGGACACTAATGGGCGTGTATTCAGAGCCTCGCCCCATTGGCACCAGATACCTG 2193
AAV4capNucl 2131 TGGGCTCCCGATGCGGGCTGGGAAATACACTGAGCCTATCGGTATCGGTACCCGCTACCTC 2190
                 *   ** **  **  *   ** *    *** *  * ***  *   ** **  ** *****
```

Figure 1B-7

```
AAV2capNuc  2194  ACTCGTAATCTGTAA  2208
AAV4capNuc1 2191  ACCCACCACCTGTAA  2205
                  ** * * ******
```

TPP1 expression in Cln2−/− dog after AAV delivery

Effect of AAV.TPP1 on autofluorescence

Control

AAV2/2.TPP1

Figure 14

Human TPP1 amino acid sequence:

MGLQACLLGLFALILSGKCSYSPEPDQRRTLPPGWVSLGRADPEEELSLTFALRQQNVERLSEL
VQAVSDPSSPQYGKYLTLENVADLVRPSPLTLHTVQKWLLAAGAQKCHSVITQDFLTCWLSIRQ
AELLLPGAEFHHYVGGPTETHVVRSPHPYQLPQALAPHVDFVGGLHHFPPTSSLRQRPEPQVTG
TVGLHLGVTPSVIRKRYNLTSQDVGSTSNNSQACAQFLEQYFHDSDLAQFMRLFGGNFAHQAS
VARVVGQQGRGRAGIEASLDVQYLMSAGANISTWVYSSPGRHEGQEPFLQWLMLLSNESALPHV
HTVSYGDDEDSLSSAYIQRVNTELMKAAARGLTLLFASGDSGAGCWSVSGRHQFRPTFPASSPY
VTTVGGTSFQEPFLITNEIVDYISGGGFSNVFPRPSYQEEAVTKFLSSSPHLPPSSYFNASGRA
YPDVAALSDGYWVVSNRVPIPWVSGTSASTPVFGGILSLINEHRILSGRPPLGFLNPRLYQQHG
AGLFDVTRGCHESCLDEEVEGQGFCSGPGWDPVTGWGTPNFPALLKTLLNP

Figure 15A - Human TPP1 nucleic acid sequence:

```
   1 cgcggaaggg cagaatggga ctccaagcct gcctcctagg gctctttgcc ctcatcctct
  61 ctggcaaatg cagttacagc ccggagcccg accagcggag gacgctgccc ccaggctggg
 121 tgtccctggg ccgtgcggac cctgaggaag agctgagtct cacctttgcc ctgagacagc
 181 agaatgtgga aagactctcg gagctggtgc aggctgtgtc ggatcccagc tctcctcaat
 241 acggaaaata cctgacccta gagaatgtgg ctgatctggt gaggccatcc ccactgaccc
 301 tccacacggt gcaaaaatgg ctcttggcag ccggagccca gaagtgccat tctgtgatca
 361 cacaggactt tctgacttgc tggctgagca tccgacaagc agagctgctg ctccctgggg
 421 ctgagtttca tcactatgtg ggaggaccta cggaaaccca tgttgtaagg tccccacatc
 481 cctaccagct tccacaggcc ttggcccccc atgtggactt tgtggggga ctgcaccatt
 541 ttcccccaac atcatccctg aggcaacgtc ctgagccgca ggtgacaggg actgtaggcc
 601 tgcatctggg ggtaaccccc tctgtgatcc gtaagcgata caacttgacc tcacaagacg
 661 tgggctctgg caccagcaat aacagccaag cctgtgccca gttcctggag cagtatttcc
 721 atgactcaga cctggctcag ttcatgcgcc tcttcggtgg caactttgca catcaggcat
 781 cagtagcccg tgtggttgga caacagggcc ggggccgggc cgggattgag gccagtctag
 841 atgtgcagta cctgatgagt gctggtgcca acatctccac ctgggtctac agtagccctg
 901 gccggcatga gggacaggag cccttcctgc agtggctcat gctgctcagt aatgagtcag
 961 ccctgccaca tgtgcatact gtgagctatg gagatgatga ggactccctc agcagcgcct
1021 acatccagcg ggtcaacact gagctcatga aggctgctgc tcgggtctc accctgctct
1081 tcgcctcagg tgacagtggg gccgggtgtt ggtctgtctc tggaagacac cagttccgcc
1141 ctaccttccc tgcctccagc ccctatgtca ccacagtggg aggcacatcc ttccaggaac
1201 ctttcctcat cacaaatgaa attgttgact atatcagtgg tggtggcttc agcaatgtgt
1261 tcccacggcc ttcataccag gaggaagctg taacgaagtt cctgagctct agcccccacc
1321 tgccaccatc cagttacttc aatgccagtg gccgtgccta cccagatgtg gctgcactttt
1381 ctgatggcta ctgggtggtc agcaacagag tgcccattcc atgggtgtcc ggaacctcgg
1441 cctctactcc agtgtttggg gggatcctat ccttgatcaa tgagcacagg atccttagtg
1501 gccgccccc tcttggcttt ctcaacccaa ggctctacca gcagcatggg gcaggactct
1561 ttgatgtaac ccgtggctgc catgagtcct gtctggatga agaggtagag ggccagggtt
1621 tctgctctgg tcctggctgg gatcctgtaa caggctgggg aacacccaac ttcccagctt
1681 tgctgaagac tctactcaac ccctgaccct tcctatcag gagagatggc ttgtccctg
1741 ccctgaagct ggcagttcag tcccttattc tgccctgttg gaagccctgc tgaaccctca
1801 actattgact gctgcagaca gcttatctcc ctaaccctga aatgctgtga gcttgacttg
1861 actccaaccc ctaccatgct ccatcatact caggtctccc tactcctgcc ttagattcct
1921 caataagatg ctgtaactag cattttttga atgcctctcc ctccgcatct catctttctc
1981 ttttcaatca ggcttttcca aagggttgta tacagactct gtgcactatt tcacttgata
```

Figure 15B - Human TPP1 nucleic acid sequence (cont.):

```
2041 ttcattcccc aattcactgc aaggagacct ctactgtcac cgtttactct ttcctaccct
2101 gacatccaga aacaatggcc tccagtgcat acttctcaat ctttgcttta tggcctttcc
2161 atcatagttg cccactccct ctccttactt agcttccagg tcttaacttc tctgactact
2221 cttgtcttcc tctctcatca atttctgctt cttcatggaa tgctgacctt cattgctcca
2281 tttgtagatt tttgctcttc tcagtttact cattgtcccc tggaacaaat cactgacatc
2341 tacaaccatt accatctcac taaataagac tttctatcca ataatgattg atacctcaaa
2401 tgtaagatgc gtgatactca acatttcatc gtccaccttc ccaaccccaa acaattccat
2461 ctcgtttctt cttggtaaat gatgctatgc tttttccaac caagccagaa acctgtgtca
2521 tcttttcacc ccaccttcaa tcaacaagtc ctcaatcaac aagtcctact gactgcacat
2581 cttaaatata tctttatcag tccacaagtc cttccaatta tatttcccaa gtatatctag
2641 aacttatcca cttatatccc cactgctact accttagttt agggctatat tctcttgaaa
2701 aaaagtgtcc ttacttcctg ccaatcccca agtcatcttc cagagtaaaa tgcaaatccc
2761 atcaggccac ttggatgaaa acccttcaag gattactgga tagaattcag gctttcccct
2821 ccagccccca atcatagctc acaaaccttc cttgctattt gttcttaagt aaaaaatcat
2881 ttttcctcct ccctccccaa accccaagga actctcactc ttgctcaagc tgttccgtcc
2941 ccttaccacc cctgatacaa ctgccaggtt aatttccaga attcttgcaa gactcagttc
3001 agaagtcacc ttctttcgtg aatgttttga ttccctgagg ctactttatt ttggtatggc
3061 tgaaaaatcc tagattttct aaacaaaacc tgtttgaatc ttggttctga tatggactag
3121 gagagagact gggtcaagta agcttatctc cctgaggctg tttcctcgtc tgttaagtgt
3181 gaatatcaat acctgccttt cataatcacc agggaataaa gtggaataat gttgataaca
3241 gtgcttggca cctggaagta ggtggcagat gttaacgccc ttcctccctt gcactgcgcc
3301 ccctgtgcct acctctagca ttgtaacgac cacatagtat tgaaatggcc agtttacttg
3361 tctgccttcc tttccaagac cgttggtgcc tagaggacta gaatcgtgtc ctatttaact
3421 ttgtgttccc aggtcctagc tcaggagttg gcaaataaga attaaatgtc tgctacaccg
3481 aaacaaa
```

Figure 16 - Macaca mulatta (Rhesus macaque) TTP1 sequence

```
        10         20         30         40         50         60
QAGFATADHS SQETETEKAM DRLARGAQSV PNDSPAQGEG THSEEEGFAM DEEDSDGELN 70         80         90        100        110        120
TWELSEGTNC PPKEQPGDIF NEDWDLELKA DQGNPYDADD IQESISQELK PWVCCAPQGD 130        140        150
```
MIYDPSWHHP PPLIPHYSKM VFETGQFDDA ED

Figure 17 -- Macaca fascicularis (Crab-eating macaque) (Cynomolgus monkey) TTP1 sequence

```
        10         20         30         40         50         60
QAGFATADHS SQERETEKAM DRLARGAQSV PNDSPARGEG THSEEEGFAM DEEDSDGELN 70         80         90        100        110        120
TWELSEGTNC PPKEQPGDIF NEDWDLELKA DQGNPYDADD IQESISQELK PWVCCAPQGD 130        140        150
```
MIYDPSWHHP PPLIPHYSKM VFETGQFDDA ED

SEQUENCE LISTING

```
<160> NUMBER OF SEQ ID NOS: 8

<210> SEQ ID NO 1
<211> LENGTH: 735
<212> TYPE: PRT
<213> ORGANISM: Adeno-associated virus

<400> SEQUENCE: 1

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140
```

```
Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
        210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
        290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
        530                 535                 540

Gln Gly Ser Glu Lys Thr Asn Val Asp Ile Glu Lys Val Met Ile Thr
545                 550                 555                 560
```

```
Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 2
<211> LENGTH: 734
<212> TYPE: PRT
<213> ORGANISM: Adeno-associated virus

<400> SEQUENCE: 2

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

Tyr Lys Tyr Leu Gly Pro Gly Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
        115                 120                 125

Gly Leu Val Glu Gln Ala Gly Glu Thr Ala Pro Gly Lys Lys Arg Pro
    130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Lys Leu Val Phe Glu Asp Glu Thr
                165                 170                 175

Gly Ala Gly Asp Gly Pro Pro Glu Gly Ser Thr Ser Gly Ala Met Ser
            180                 185                 190

Asp Asp Ser Glu Met Arg Ala Ala Ala Gly Gly Ala Val Glu Gly
        195                 200                 205
```

```
Gly Gln Gly Ala Asp Gly Val Gly Asn Ala Ser Gly Asp Trp His Cys
    210                 215                 220

Asp Ser Thr Trp Ser Glu Gly His Val Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Met Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Leu Val Thr Gly Asn Thr Ser Gln Gln Gln Thr Asp Arg Asn
370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
        435                 440                 445

Asn Ala Gly Thr Ala Thr Thr Asn Phe Thr Lys Leu Arg Pro Thr Asn
450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
            500                 505                 510

Arg Trp Ser Ala Leu Thr Pro Gly Pro Pro Met Ala Thr Ala Gly Pro
        515                 520                 525

Ala Asp Ser Lys Phe Ser Asn Ser Gln Leu Ile Phe Ala Gly Pro Lys
530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
        595                 600                 605

Asp Ile Tyr Tyr Gln Gly Pro Ile Trp Ala Lys Ile Pro His Thr Asp
610                 615                 620
```

| | | | | | | | | | | | |
|---|---|---|---|---|---|---|---|---|---|---|---|
|Gly|His|Phe|His|Pro|Ser|Pro|Leu|Ile|Gly|Phe|Gly|Leu|Lys|His|
|625| | | | |630| | | |635| | | | |640|

| | | | | | | | | | | | |
|---|---|---|---|---|---|---|---|---|---|---|---|
|Pro|Pro|Pro|Gln|Ile|Phe|Ile|Lys|Asn|Thr|Pro|Val|Pro|Ala|Asn|Pro|
| | | | |645| | | | |650| | | | |655| |

Ala Thr Thr Phe Ser Ser Thr Pro Val Asn Ser Phe Ile Thr Gln Tyr
            660                 665                 670

Ser Thr Gly Gln Val Ser Val Gln Ile Asp Trp Glu Ile Gln Lys Glu
        675                 680                 685

Arg Ser Lys Arg Trp Asn Pro Glu Val Gln Phe Thr Ser Asn Tyr Gly
690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                725                 730

<210> SEQ ID NO 3
<211> LENGTH: 2208
<212> TYPE: DNA
<213> ORGANISM: Adeno-associated virus

<400> SEQUENCE: 3

```
atggctgccg atggttatct tccagattgg ctcgaggaca ctctctctga aggaataaga      60
cagtggtgga agctcaaacc tggcccacca ccaccaaagc ccgcagagcg cataaggac     120
gacagcaggg gtcttgtgct tcctgggtac aagtacctcg acccttcaa cggactcgac     180
aagggagagc cggtcaacga ggcagacgcc gcggccctcg agcacgacaa agcctacgac    240
cggcagctcg acagcggaga caacccgtac ctcaagtaca accacgccga cgcggagttt    300
caggagcgcc ttaaagaaga tacgtctttt gggggcaacc tcggacgagc agtcttccag    360
gcgaaaaaga gggttcttga acctctgggc ctggttgagg aacctgttaa cggctccg     420
ggaaaaaaga ggccggtaga gcactctcct gtggagccag actcctcctc gggaaccgga    480
aaggcgggcc agcagcctgc aagaaaaaga ttgaattttg gtcagactgg agacgcagac    540
tcagtacctg accccagcc ctcgacag ccaccagcag cccctctgg tctgggaact    600
aatacgatgg ctacaggcag tggcgcacca atggcagaca taacgagg cgccgacgga    660
gtgggtaatt cctcgggaaa ttggcattgc gattccacat ggatgggcga cagagtcatc    720
accaccagca cccgaacctg gcccctgccc acctacaaca accacctcta caaacaaatt    780
tccagccaat caggagcctc gaacgacaat cactactttg ctacagcac cccttggggg    840
tattttgact tcaacagatt ccactgccac ttttcaccac gtgactggca agactcatc    900
aacaacaact ggggattccg acccaagaga ctcaacttca gctctttaa cattcaagtc    960
aaagaggtca cgcagaatga cggtacgacg acgattgcca ataacttac cagcacggtt   1020
caggtgttta ctgactcgga gtaccagctc ccgtacgtcc tcggctcggc gcatcaagga   1080
tgcctcccgc cgttcccagc agacgtcttc atggtgccac agtatggata cctcaccctg   1140
aacaacggga gtcaggcagt aggacgctct tcatttact gcctggagta ctttcctct   1200
cagatgctgc gtaccggaaa caactttacc ttcagctaca cttttgagga cgttcctttc   1260
cacagcagct acgctcacag ccagagtctg accgtctca tgaatcctct catcgaccag   1320
tacctgtatt acttgagcag aacaaacact ccaagtggaa ccaccacgca gtcaaggctt   1380
cagttttctc aggccggagc gagtgacatt cgggaccagt ctaggaactg gcttcctgga   1440
ccctgttacc gccagcagcg agtatcaaag acatctgcgg ataacaacaa cagtgaatac   1500
```

| | |
|---|---|
| tcgtggactg gagctaccaa gtaccacctc aatggcagag actctctggt gaatccgggc | 1560 |
| ccggccatgg caagccacaa ggacgatgaa gaaaagtttt tcctcagag cggggttctc | 1620 |
| atctttggga agcaaggctc agagaaaaca atgtggaca ttgaaaaggt catgattaca | 1680 |
| gacgaagagg aaatcaggac aaccaatccc gtggctacgg agcagtatgg ttctgtatct | 1740 |
| accaacctcc agagaggcaa cagacaagca gctaccgcag atgtcaacac acaaggcgtt | 1800 |
| cttccaggca tggtctggca ggacagagat gtgtaccttc aggggcccat ctgggcaaag | 1860 |
| attccacaca cggacggaca ttttcacccc tctcccctca tgggtggatt cggacttaaa | 1920 |
| caccctcctc cacagattct catcaagaac accccggtac ctgcgaatcc ttcgaccacc | 1980 |
| ttcagtgcgg caaagtttgc ttccttcatc acacagtact ccacgggaca ggtcagcgtg | 2040 |
| gagatcgagt gggagctgca gaaggaaaac agcaaacgct ggaatcccga aattcagtac | 2100 |
| acttccaact acaacaagtc tgttaatgtg gactttactg tggacactaa tggcgtgtat | 2160 |
| tcagagcctc gccccattgg caccagatac ctgactcgta atctgtaa | 2208 |

<210> SEQ ID NO 4
<211> LENGTH: 2205
<212> TYPE: DNA
<213> ORGANISM: Adeno-associated virus

<400> SEQUENCE: 4

| | |
|---|---|
| atgactgacg gttaccttcc agattggcta gaggacaacc tctctgaagg cgttcgagag | 60 |
| tggtgggcgc tgcaacctgg agcccctaaa cccaaggcaa atcaacaaca tcaggacaac | 120 |
| gctcggggtc ttgtgcttcc gggttacaaa tacctcggac ccgcaacgg actcgacaag | 180 |
| ggggaacccg tcaacgcagc ggacgcggca gccctcgagc acgacaaggc ctacgaccag | 240 |
| cagctcaagg ccggtgacaa ccctacctc aagtacaacc acgccgacgc ggagttccag | 300 |
| cagcggcttc agggcgacac atcgtttggg ggcaacctcg gcagagcagt cttccaggcc | 360 |
| aaaaagaggg ttcttgaacc tcttggtctg gttgagcaag cgggtgagac ggctcctgga | 420 |
| aagaagagac cgttgattga atccccccag cagcccgact cctccacggg tatcggcaaa | 480 |
| aaaggcaagc agccggctaa aaagaagctc gttttcgaag acgaaactgg agcaggcgac | 540 |
| ggaccccctg agggatcaac ttccggagcc atgtctgatg acagtgagat cgtgcagca | 600 |
| gctggcggag ctgcagtcga gggcggacaa ggtgccgatg gagtgggtaa tgcctcgggt | 660 |
| gattggcatt gcgattccac ctggtctgag ggccacgtca cgaccaccag caccagaacc | 720 |
| tgggtcttgc ccacctacaa caaccacctc tacaagcgac tcggagagag cctgcagtcc | 780 |
| aacacctaca acggattctc caccccctgg ggatactttg acttcaaccg cttccactgc | 840 |
| cacttctcac cacgtgactg gcagcgactc atcaacaaca ctggggcat gcgacccaaa | 900 |
| gccatgcggg tcaaaatctt caacatccag gtcaaggagg tcacgacgtc gaacggcgag | 960 |
| acaacggtgg ctaataaccc taccagcacg gttcagatct ttgcggactc gtcgtacgaa | 1020 |
| ctgccgtacg tgatggatgc gggtcaagag gcagcctgc tcctttttcc caacgacgtc | 1080 |
| tttatggtgc cccagtacgg ctactgtgga ctggtgaccg gcaacacttc gcagcaacag | 1140 |
| actgacagaa atgccttcta ctgcctggag tactttcctt cgcagatgct gcggactggc | 1200 |
| aacaactttg aaattacgta cagttttgag aaggtgcctt ccactcgat gtacgcgcac | 1260 |
| agccagagcc tggaccggct gatgaaccct ctcatcgacc agtacctgtg gggactgcaa | 1320 |
| tcgaccacca ccggaaccac cctgaatgcc gggactgcca ccaccaactt taccaagctg | 1380 |
| cggcctacca acttttccaa ctttaaaaag aactggctgc ccgggccttc aatcaagcag | 1440 |

```
caggcttct caaagactgc caatcaaaac tacaagatcc ctgccaccgg gtcagacagt    1500
ctcatcaaat acgagacgca cagcactctg gacggaagat ggagtgccct gaccccgga    1560
cctccaatgg ccacggctgg acctgcggac agcaagttca gcaacagcca gctcatcttt    1620
gcggggccta acagaacgg caacacggcc accgtacccg ggactctgat cttcacctct    1680
gaggaggagc tggcagccac caacgccacc gatacggaca tgtggggcaa cctacctggc    1740
ggtgaccaga gcaacagcaa cctgccgacc gtggacagac tgacagcctt gggagccgtg    1800
cctggaatgg tctggcaaaa cagagacatt tactaccagg gtcccatttg gccaagatt    1860
cctcataccg atggacactt tcacccctca ccgctgattg gtgggtttgg gctgaaacac    1920
ccgcctcctc aaatttttat caagaacacc ccggtacctg cgaatcctgc aacgacttc    1980
agctctactc cggtaaactc cttcattact cagtacagca ctggccaggt gtcggtgcag    2040
attgactggg agatccagaa ggagcggtcc aaacgctgga accccgaggt ccagtttacc    2100
tccaactacg acagcaaaaa ctctctgttg tgggctcccg atgcggctgg gaaatacact    2160
gagcctaggg ctatcggtac ccgctacctc acccaccacc tgtaa                   2205
```

<210> SEQ ID NO 5
<211> LENGTH: 563
<212> TYPE: PRT
<213> ORGANISM: Homo sapiens

<400> SEQUENCE: 5

```
Met Gly Leu Gln Ala Cys Leu Leu Gly Leu Phe Ala Leu Ile Leu Ser
1               5                   10                  15

Gly Lys Cys Ser Tyr Ser Pro Glu Pro Asp Gln Arg Arg Thr Leu Pro
                20                  25                  30

Pro Gly Trp Val Ser Leu Gly Arg Ala Asp Pro Glu Glu Glu Leu Ser
            35                  40                  45

Leu Thr Phe Ala Leu Arg Gln Gln Asn Val Glu Arg Leu Ser Glu Leu
        50                  55                  60

Val Gln Ala Val Ser Asp Pro Ser Ser Pro Gln Tyr Gly Lys Tyr Leu
65                  70                  75                  80

Thr Leu Glu Asn Val Ala Asp Leu Val Arg Pro Ser Pro Leu Thr Leu
                85                  90                  95

His Thr Val Gln Lys Trp Leu Leu Ala Ala Gly Ala Gln Lys Cys His
            100                 105                 110

Ser Val Ile Thr Gln Asp Phe Leu Thr Cys Trp Leu Ser Ile Arg Gln
        115                 120                 125

Ala Glu Leu Leu Leu Pro Gly Ala Glu Phe His His Tyr Val Gly Gly
    130                 135                 140

Pro Thr Glu Thr His Val Val Arg Ser Pro His Pro Tyr Gln Leu Pro
145                 150                 155                 160

Gln Ala Leu Ala Pro His Val Asp Phe Val Gly Gly Leu His His Phe
                165                 170                 175

Pro Pro Thr Ser Ser Leu Arg Gln Arg Pro Glu Pro Gln Val Thr Gly
            180                 185                 190

Thr Val Gly Leu His Leu Gly Val Thr Pro Ser Val Ile Arg Lys Arg
        195                 200                 205

Tyr Asn Leu Thr Ser Gln Asp Val Gly Ser Gly Thr Ser Asn Asn Ser
    210                 215                 220

Gln Ala Cys Ala Gln Phe Leu Glu Gln Tyr Phe His Asp Ser Asp Leu
225                 230                 235                 240
```

Ala Gln Phe Met Arg Leu Phe Gly Gly Asn Phe Ala His Gln Ala Ser
        245                 250                 255

Val Ala Arg Val Val Gly Gln Gln Gly Arg Gly Arg Ala Gly Ile Glu
        260                 265                 270

Ala Ser Leu Asp Val Gln Tyr Leu Met Ser Ala Gly Ala Asn Ile Ser
        275                 280                 285

Thr Trp Val Tyr Ser Ser Pro Gly Arg His Glu Gly Gln Glu Pro Phe
        290                 295                 300

Leu Gln Trp Leu Met Leu Leu Ser Asn Glu Ser Ala Leu Pro His Val
305                 310                 315                 320

His Thr Val Ser Tyr Gly Asp Asp Glu Asp Ser Leu Ser Ser Ala Tyr
            325                 330                 335

Ile Gln Arg Val Asn Thr Glu Leu Met Lys Ala Ala Arg Gly Leu
        340                 345                 350

Thr Leu Leu Phe Ala Ser Gly Asp Ser Gly Ala Gly Cys Trp Ser Val
            355                 360                 365

Ser Gly Arg His Gln Phe Arg Pro Thr Phe Pro Ala Ser Ser Pro Tyr
    370                 375                 380

Val Thr Thr Val Gly Gly Thr Ser Phe Gln Glu Pro Phe Leu Ile Thr
385                 390                 395                 400

Asn Glu Ile Val Asp Tyr Ile Ser Gly Gly Gly Phe Ser Asn Val Phe
            405                 410                 415

Pro Arg Pro Ser Tyr Gln Glu Glu Ala Val Thr Lys Phe Leu Ser Ser
        420                 425                 430

Ser Pro His Leu Pro Pro Ser Ser Tyr Phe Asn Ala Ser Gly Arg Ala
        435                 440                 445

Tyr Pro Asp Val Ala Ala Leu Ser Asp Gly Tyr Trp Val Val Ser Asn
450                 455                 460

Arg Val Pro Ile Pro Trp Val Ser Gly Thr Ser Ala Ser Thr Pro Val
465                 470                 475                 480

Phe Gly Gly Ile Leu Ser Leu Ile Asn Glu His Arg Ile Leu Ser Gly
            485                 490                 495

Arg Pro Pro Leu Gly Phe Leu Asn Pro Arg Leu Tyr Gln Gln His Gly
        500                 505                 510

Ala Gly Leu Phe Asp Val Thr Arg Gly Cys His Glu Ser Cys Leu Asp
        515                 520                 525

Glu Glu Val Glu Gly Gln Gly Phe Cys Ser Gly Pro Gly Trp Asp Pro
530                 535                 540

Val Thr Gly Trp Gly Thr Pro Asn Phe Pro Ala Leu Leu Lys Thr Leu
545                 550                 555                 560

Leu Asn Pro

<210> SEQ ID NO 6
<211> LENGTH: 3487
<212> TYPE: DNA
<213> ORGANISM: Homo sapiens

<400> SEQUENCE: 6
cgcggaaggg cagaatggga ctccaagcct gcctcctagg gctctttgcc ctcatcctct     60
ctggcaaatg cagttacagc ccggagcccg accagcggag gacgctgccc ccaggctggg    120
tgtccctggg ccgtgcggac cctgaggaag agctgagtct caccttgcc ctgagacagc     180 agaatgtgga aagactctcg gagctggtgc aggctgtgtc ggatcccagc tctcctcaat    240

-continued

```
acggaaaata cctgaccsta gagaatgtgg ctgatctggt gaggccatcc ccactgaccc    300
tccacacggt gcaaaaatgg ctcttggcag ccggagccca gaagtgccat tctgtgatca    360
cacaggactt tctgacttgc tggctgagca tccgacaagc agagctgctg ctccctgggg    420
ctgagtttca tcactatgtg ggaggaccta cggaaaccca tgttgtaagg tccccacatc    480
cctaccagct tccacaggcc ttggcccccc atgtggactt tgtgggggga ctgcaccatt    540
ttcccccaac atcatccctg aggcaacgtc ctgagccgca ggtgacaggg actgtaggcc    600
tgcatctggg ggtaaccccc tctgtgatcc gtaagcgata caacttgacc tcacaagacg    660
tgggctctgg caccagcaat aacagccaag cctgtgccca gttcctggag cagtatttcc    720
atgactcaga cctggctcag ttcatgcgcc tcttcggtgg caactttgca catcaggcat    780
cagtagcccg tgtggttgga caacagggcc ggggccgggc cgggattgag gccagtctag    840
atgtgcagta cctgatgagt gctggtgcca acatctccac ctgggtctac agtagccctg    900
gccggcatga gggacaggag cccttcctgc agtggctcat gctgctcagt aatgagtcag    960
ccctgccaca tgtgcatact gtgagctatg agatgatga ggactccctc agcagcgcct   1020
acatccagcg ggtcaacact gagctcatga aggctgctgc tcggggtctc accctgctct   1080
tcgcctcagg tgacagtggg gccgggtgtt ggtctgtctc tggaagacac cagttccgcc   1140
ctaccttccc tgcctccagc ccctatgtca ccacagtggg aggcacatcc ttccaggaac   1200
cttttcctcat cacaaatgaa attgttgact atatcagtgg tggtggcttc agcaatgtgt   1260
tcccacggcc ttcataccag gaggaagctg taacgaagtt cctgagctct agccccacc   1320
tgccaccatc cagttacttc aatgccagtg gccgtgccta cccagatgtg ctgcactttt   1380
ctgatggcta ctgggtggtc agcaacagag tgcccattcc atgggtgtcc ggaacctcgg   1440
cctctactcc agtgtttggg gggatcctat ccttgatcaa tgagcacagg atccttagtg   1500
gccgcccccc tcttggcttt ctcaacccaa ggctctacca gcagcatggg gcaggactct   1560
ttgatgtaac ccgtgctgc catgagtcct gtctggatga agaggtagag gccagggtt   1620
tctgctctgg tcctggctgg atcctgtaa caggctgggg aacacccaac ttcccagctt   1680
tgctgaaagac tctactcaac ccctgaccct ttcctatcag gagagatggc ttgtcccctg   1740
ccctgaagct ggcagttcag tcccttattc tgccctgttg gaagccctgc tgaaccctca   1800
actattgact gctgcagaca gcttatctcc ctaaccctga aatgctgtga gcttgacttg   1860
actcccaacc ctaccatgct ccatcatact caggtctccc tactcctgcc ttagattcct   1920
caataagatg ctgtaactag catttttttga atgcctctcc ctccgcatct catctttctc   1980
ttttcaatca ggcttttcca aagggttgta tacagactct gtgcactatt tcacttgata   2040
ttcattcccc aattcactgc aaggagacct ctactgtcac cgtttactct ttcctacccct  2100
gacatccaga aacaatggcc tccagtgcat acttctcaat ctttgcttta tggcctttcc   2160
atcatagttg cccactccct ctccttactt agcttccagg tcttaacttc tctgactact   2220
cttgtcttcc tctctcatca atttctgctt cttcatggaa tgctgacctt cattgctcca   2280
tttgtagatt tttgctcttc tcagtttact cattgtcccc tggaacaaat cactgacatc   2340
tacaaccatt accatctcac taaataagac tttctatcca ataatgattg atacctcaaa   2400
tgtaagatgc gtgatactca acatttcatc gtccaccttc ccaacccccaa acaattccat  2460
ctcgtttctt cttggtaaat gatgctatgc ttttccaac caagccagaa acctgtgtca   2520
tcttttcacc ccaccttcaa tcaacaagtc ctcaatcaac aagtcctact gactgcacat   2580
cttaaatata tctttatcag tccacaagtc cttccaatta tatttcccaa gtatatctag   2640
```

```
aacttatcca cttatatccc cactgctact accttagttt agggctatat tctcttgaaa    2700
aaaagtgtcc ttacttcctg ccaatcccca agtcatcttc cagagtaaaa tgcaaatccc    2760
atcaggccac ttggatgaaa acccttcaag gattactgga tagaattcag gctttcccct    2820
ccagccccca atcatagctc acaaaccttc cttgctattt gttcttaagt aaaaaatcat    2880
ttttcctcct ccctccccaa acccaagga actctcactc ttgctcaagc tgttccgtcc    2940
ccttaccacc cctgatacaa ctgccaggtt aatttccaga attcttgcaa gactcagttc    3000
agaagtcacc ttctttcgtg aatgttttga ttccctgagg ctactttatt ttggtatggc    3060
tgaaaaatcc tagattttct aaacaaaacc tgtttgaatc ttggttctga tatggactag    3120
gagagagact gggtcaagta agcttatctc cctgaggctg tttcctcgtc tgttaagtgt    3180
gaatatcaat acctgccttt cataatcacc agggaataaa gtggaataat gttgataaca    3240
gtgcttggca cctggaagta ggtggcagat gttaacgccc ttcctccctt gcactgcgcc    3300
ccctgtgcct acctctagca ttgtaacgac cacatagtat tgaaatggcc agtttacttg    3360
tctgccttcc tttccaagac cgttggtgcc tagaggacta gaatcgtgtc ctatttaact    3420
ttgtgttccc aggtcctagc tcaggagttg gcaaataaga attaaatgtc tgctacaccg    3480
aaacaaa                                                              3487
```

<210> SEQ ID NO 7
<211> LENGTH: 152
<212> TYPE: PRT
<213> ORGANISM: Macaca mulatta

<400> SEQUENCE: 7

Gln Ala Gly Phe Ala Thr Ala Asp His Ser Ser Gln Glu Thr Glu Thr
1               5                   10                  15

Glu Lys Ala Met Asp Arg Leu Ala Arg Gly Ala Gln Ser Val Pro Asn
                20                  25                  30

Asp Ser Pro Ala Gln Gly Glu Gly Thr His Ser Glu Glu Glu Gly Phe
            35                  40                  45

Ala Met Asp Glu Glu Asp Ser Asp Gly Glu Leu Asn Thr Trp Glu Leu
        50                  55                  60

Ser Glu Gly Thr Asn Cys Pro Pro Lys Glu Gln Pro Gly Asp Ile Phe
65                  70                  75                  80

Asn Glu Asp Trp Asp Leu Glu Leu Lys Ala Asp Gln Gly Asn Pro Tyr
                85                  90                  95

Asp Ala Asp Asp Ile Gln Glu Ser Ile Ser Gln Glu Leu Lys Pro Trp
            100                 105                 110

Val Cys Cys Ala Pro Gln Gly Asp Met Ile Tyr Asp Pro Ser Trp His
        115                 120                 125

His Pro Pro Leu Ile Pro His Tyr Ser Lys Met Val Phe Glu Thr
130                 135                 140

Gly Gln Phe Asp Asp Ala Glu Asp
145                 150

<210> SEQ ID NO 8
<211> LENGTH: 152
<212> TYPE: PRT
<213> ORGANISM: Macaca fascicularis

<400> SEQUENCE: 8

Gln Ala Gly Phe Ala Thr Ala Asp His Ser Ser Gln Glu Arg Glu Thr
1               5                   10                  15

-continued

```
Glu Lys Ala Met Asp Arg Leu Ala Arg Gly Ala Gln Ser Val Pro Asn
         20                  25                  30

Asp Ser Pro Ala Arg Gly Glu Gly Thr His Ser Glu Glu Glu Gly Phe
         35                  40                  45

Ala Met Asp Glu Glu Asp Ser Asp Gly Glu Leu Asn Thr Trp Glu Leu
         50                  55                  60

Ser Glu Gly Thr Asn Cys Pro Pro Lys Glu Gln Pro Gly Asp Ile Phe
65                       70                  75                  80

Asn Glu Asp Trp Asp Leu Glu Leu Lys Ala Asp Gln Gly Asn Pro Tyr
                 85                  90                  95

Asp Ala Asp Asp Ile Gln Glu Ser Ile Ser Gln Glu Leu Lys Pro Trp
                 100                 105                 110

Val Cys Cys Ala Pro Gln Gly Asp Met Ile Tyr Asp Pro Ser Trp His
         115                 120                 125

His Pro Pro Pro Leu Ile Pro His Tyr Ser Lys Met Val Phe Glu Thr
         130                 135                 140

Gly Gln Phe Asp Asp Ala Glu Asp
145                 150
```

METHODS AND COMPOSITIONS FOR TREATING BRAIN DISEASES

RELATED APPLICATION

This application claims priority to U.S. Provisional Patent Application No. 61/859,157, filed Jul. 26, 2013, the entirety of which is incorporated herein by reference.

SEQUENCE LISTING

The instant application contains a Sequence Listing which has been submitted electronically in ASCII format and is hereby incorporated by reference in its entirety. Said ASCII copy, created on Aug. 13, 2014, is named 17023_139WO1_SL.txt and is 30,720 bytes in size.

BACKGROUND

Gene transfer is now widely recognized as a powerful tool for analysis of biological events and disease processes at both the cellular and molecular level. More recently, the application of gene therapy for the treatment of human diseases, either inherited (e.g., ADA deficiency) or acquired (e.g., cancer or infectious disease), has received considerable attention. With the advent of improved gene transfer techniques and the identification of an ever expanding library of defective gene-related diseases, gene therapy has rapidly evolved from a treatment theory to a practical reality.

Traditionally, gene therapy has been defined as a procedure in which an exogenous gene is introduced into the cells of a patient in order to correct an inborn genetic error. Although more than 4500 human diseases are currently classified as genetic, specific mutations in the human genome have been identified for relatively few of these diseases. Until recently, these rare genetic diseases represented the exclusive targets of gene therapy efforts. Accordingly, most of the NIH approved gene therapy protocols to date have been directed toward the introduction of a functional copy of a defective gene into the somatic cells of an individual having a known inborn genetic error. Only recently, have researchers and clinicians begun to appreciate that most human cancers, certain forms of cardiovascular disease, and many degenerative diseases also have important genetic components, and for the purposes of designing novel gene therapies, should be considered "genetic disorders." Therefore, gene therapy has more recently been broadly defined as the correction of a disease phenotype through the introduction of new genetic information into the affected organism.

In in vivo gene therapy, a transferred gene is introduced into cells of the recipient organism in situ that is, within the recipient. In vivo gene therapy has been examined in several animal models. Several recent publications have reported the feasibility of direct gene transfer in situ into organs and tissues such as muscle, hematopoietic stem cells, the arterial wall, the nervous system, and lung. Direct injection of DNA into skeletal muscle, heart muscle and injection of DNA-lipid complexes into the vasculature also has been reported to yield a detectable expression level of the inserted gene product(s) in vivo. Treatment of diseases of the central nervous system, e.g., inherited genetic diseases of the brain, remains an intractable problem. Examples of such are the lysosomal storage diseases and Alzheimer's disease. Collectively, the incidence of lysosomal storage diseases (LSD) is 1 in 10,000 births world wide, and in 65% of cases, there is significant central nervous system (CNS) involvement. Proteins deficient in these disorders, when delivered intravenously, do not cross the blood-brain barrier, or, when delivered directly to the brain, are not widely distributed. Thus, therapies for the CNS deficits need to be developed.

SUMMARY

The present invention provides a method of delivering a therapeutic agent (e.g., protein or nucleic acid) to the central nervous system of a mammal, comprising administering to the mammal's cisterna magna an rAAV particle comprising an AAV capsid protein and a vector comprising a nucleic acid encoding a therapeutic agent inserted between a pair of AAV inverted terminal repeats in a manner effective to infect cells that contact the cerebrospinal fluid (CSF) of in the mammal such that the cells express the therapeutic agent in the mammal.

The present invention provides a method of treating a disease in a mammal comprising administering to the mammal's cisterna magna an rAAV particle comprising an AAV capsid protein and a vector comprising a nucleic acid encoding a therapeutic agent (e.g., a therapeutic nucleic acid or a nucleic acid encoding a protein) inserted between a pair of AAV inverted terminal repeats in a manner effective to infect cells that contact the cerebrospinal fluid (CSF) in the mammal, wherein the cell expresses the therapeutic agent so as to treat the disease.

In certain embodiments, the AAV particle is an rAAV2 particle. As used herein, the term AAV2/1 is used to mean an AAV2 ITR and AAV1 capsid, the term AAV2/2 is an AAV2 ITR and AAV2 capsid, the term AAV2/4 is an AAV2 ITR and AAV4 capsid, etc. In certain embodiments, the AAV particle is an rAAV8 particle. In certain embodiments, the AAV particle is an rAAV9 particle. In certain embodiments, the AAV particle is an rAAVrh10 particle. In certain embodiments, the rAAV capsid has at least 80% homology to AAV2 capsid protein VP1, VP2, and/or VP3. In certain embodiments, the rAAV2 capsid has 100% homology to AAV2 capsid VP1, VP2, and/or VP3. In certain embodiments, the rAAV capsid has at least 80% homology to AAV4 capsid protein VP1, VP2, and/or VP3. In certain embodiments, the rAAV4 capsid has 100% homology to AAV4 capsid VP1, VP2, and/or VP3. In certain embodiments, the rAAV capsid has at least 80% homology to AAV9 capsid protein VP1, VP2, and/or VP3. In certain embodiments, the rAAV9 capsid has 100% homology to AAV9 capsid VP1, VP2, and/or VP3.

In certain embodiments, the rAAV particle is an rAAV2 particle that infects the non-rodent ependymal cell at an rate of more than 20% than the infectivity rate of AAV4, such as at a rate of more than 50% or 100%, 1000% or 2000% than the infectivity rate of AAV4.

In certain embodiments, the cell expresses the therapeutic agent and secretes the therapeutic agent into the CSF. In certain embodiments, the cell is an ependymal, pial, endothelial or meningeal cell. In certain embodiments, the method further comprises additionally administering the rAAV to the non-human primate's brain ventricle, subarachnoid space and/or intrathecal space.

The present invention provides a method of delivering a nucleic acid to a brain cell of a mammal comprising administering to the brain cell an AAV particle containing a vector comprising the nucleic acid inserted between a pair of AAV inverted terminal repeats, thereby delivering the nucleic acid to the brain cell. In certain embodiments, the rAAV is an rAAV2 particle that infects the brain cell at an rate of more than 20% than the infectivity rate of AAV4, such as at a rate of more than 50% or 100%, 1000% or 2000% than the infectivity rate of AAV4.

In certain embodiments, the disease is a lysosomal storage disease (LSD). In certain embodiments, the LSD is infantile or late infantile ceroid lipofuscinoses, neuronopathic Gaucher, Juvenile Batten, Fabry, MLD, Sanfilippo A, Hunter, Krabbe, Morquio, Pompe, Niemann-Pick C, Tay-Sachs, Hurler (MPS-I H), Sanfilippo B, Maroteaux-Lamy, Niemann-Pick A, Cystinosis, Hurler-Scheie (MPS-I H/S), Sly Syndrome (MPS VII), Scheie (MPS-I S), Infantile Batten, GM1 Gangliosidosis, Mucolipidosis type II/III, or Sandhoff disease. In certain embodiments, the disease is LINCL. In certain embodiments, the disease is a neurodegenerative disease, such as Alzheimer's disease, Huntington's disease, ALS, hereditary spastic hemiplegia, primary lateral sclerosis, spinal muscular atrophy, Kennedy's disease, a polyglutamine repeat disease, or Parkinson's disease.

In certain embodiments, the mammal is a non-rodent mammal, such as a primate, horse, sheep, goat, pig, or dog. In certain embodiments, the primate is a human.

In certain embodiments, the therapeutic agent is a therapeutic nucleic acid. In certain embodiments, the therapeutic agent is a protein.

In certain embodiments, the nucleic acid encodes a lysosomal hydrolase. In certain embodiments, the nucleic acid encodes TPP1.

In certain embodiments, the therapeutic protein is a protective ApoE isoform protein. As used herein, the term "protective ApoE isoform" is used to distinguish ApoE isoforms that decrease the risk of Alzheimer's disease by at least 5%, such as 10%, 20%, 30%, 40%, 50%, 60%, 70%, 80%, 90%, 100% or more.

In certain embodiments, the protective ApoE isoform has at least about 80% homology to ApoE ε2. In certain embodiments, the protective ApoE isoform has 100% homology to ApoE ε2.

In certain embodiments, the rAAV particle is injected at 1-3 locations in the brain, such as at one, two, or three locations in the brain.

BRIEF DESCRIPTION OF THE DRAWINGS

FIG. 1A is an alignment of AAV2 (SEQ ID NO:1) and AAV4 (SEQ ID NO:2) proteins and FIG. 1B is and alignment of AAV2 (SEQ ID NO:3) and AAV4 (SEQ ID NO:4) nucleotides based on the sequence from AAV2 (NC_001401) and AAV4 (NC_001829).

FIG. 14 provides the Human TPP1 amino acid sequence (SEQ ID NO:5).

FIGS. 15A and 15B together provide the Human TPP1 nucleic acid sequence (SEQ ID NO:6).

FIG. 16 provides the Macaca mulatta TPP1 amino acid sequence (SEQ ID NO:7).

FIG. 17 provides the Macaca fascicularis TPP1 amino acid sequence (SEQ ID NO:8).

DETAILED DESCRIPTION

Figure 2:
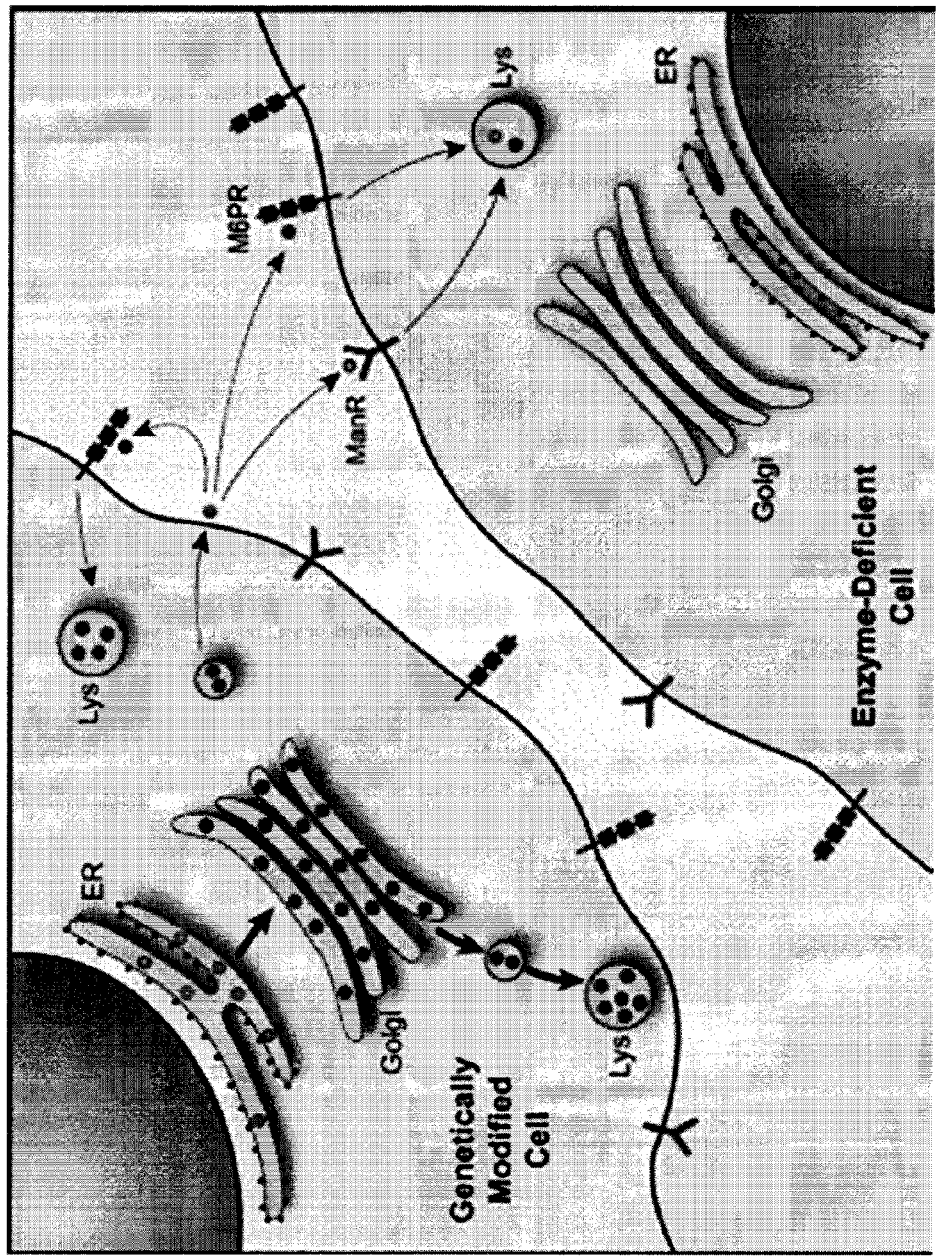
FIG. 2 shows an illustration of "cross correction" between cells. Sands and Davidson, Mol Ther 13(5):839-849, 2006.

Adeno associated virus (AAV) is a small nonpathogenic virus of the parvoviridae family. AAV is distinct from the other members of this family by its dependence upon a helper virus for replication. In the absence of a helper virus, AAV may integrate in a locus specific manner into the q arm of chromosome 19. The approximately 5 kb genome of AAV consists of one segment of single stranded DNA of either plus or minus polarity. The ends of the genome are short inverted terminal repeats which can fold into hairpin structures and serve as the origin of viral DNA replication. Physically, the parvovirus virion is non-enveloped and its icosohedral capsid is approximately 20 nm in diameter.

To-date numerous serologically distinct AAVs have been identified, and more than a dozen have been isolated from humans or primates. The genome of AAV2 is 4680 nucleotides in length and contains two open reading frames (ORFs). The left ORF encodes the non-structural Rep proteins, Rep 40, Rep 52, Rep 68 and Rep 78, which are involved in regulation of replication and transcription in addition to the production of single-stranded progeny genomes. Furthermore, two of the Rep proteins have been associated with the preferential integration of AAV genomes into a region of the q arm of human chromosome 19. Rep68/78 has also been shown to possess NTP binding activity as well as DNA and RNA helicase activities. The Rep proteins possess a nuclear localization signal as well as several potential phosphorylation sites. Mutation of one of these kinase sites resulted in a loss of replication activity.

The ends of the genome are short inverted terminal repeats (ITR) which have the potential to fold into T-shaped hairpin structures that serve as the origin of viral DNA replication. Within the ITR region two elements have been described which are central to the function of the ITR, a GAGC repeat motif and the terminal resolution site (trs). The repeat motif has been shown to bind Rep when the ITR is in either a linear or hairpin conformation. This binding serves to position Rep68/78 for cleavage at the trs which occurs in a site- and strand-specific manner. In addition to their role in replication, these two elements appear to be central to viral integration. Contained within the chromosome 19 integration locus is a Rep binding site with an adjacent trs. These elements have been shown to be functional and necessary for locus specific integration.

The AAV virion is a non-enveloped, icosohedral particle approximately 25 nm in diameter, consisting of three related proteins referred to as VP1, VP2 and VP3. The right ORF encodes the capsid proteins VP1, VP2, and VP3. These proteins are found in a ratio of 1:1:10 respectively and are all derived from the right-hand ORF. The capsid proteins differ from each other by the use of alternative splicing and an unusual start codon. Deletion analysis has shown that removal or alteration of VP1 which is translated from an alternatively spliced message results in a reduced yield of infections particles. Mutations within the VP3 coding region result in the failure to produce any single-stranded progeny DNA or infectious particles. An AAV particle is a viral particle comprising an AAV capsid protein. An AAV capsid polypeptide can encode the entire VP1, VP2 and VP3 polypeptide. The particle can be a particle comprising AAV2 and other AAV capsid proteins (i.e., a chimeric protein, such as AAV4 and AAV2). Variations in the amino acid sequence of the AAV2 capsid protein are contemplated herein, as long as the resulting viral particle comprises the AAV2 capsid remains antigenically or immunologically distinct from AAV4, as can be routinely determined by standard methods. Specifically, for example, ELISA and Western blots can be used to determine whether a viral particle is antigenically or immunologically distinct from AAV4. Furthermore, the AAV2 viral particle preferably retains tissue tropism distinct from AAV4.

An AAV2 particle is a viral particle comprising an AAV2 capsid protein. An AAV2 capsid polypeptide encoding the entire VP1, VP2, and VP3 polypeptide can overall have at least about 63% homology (or identity) to the polypeptide having the amino acid sequence encoded by nucleotides set forth in SEQ ID NO:1 (AAV2 capsid protein). The capsid protein can have about 70% homology, about 75% homology, 80% homology, 85% homology, 90% homology, 95% homology, 98% homology, 99% homology, or even 100% homology to the protein set forth in SEQ ID NO:1. The capsid protein can have about 70% identity, about 75% identity, 80% identity, 85% identity, 90% identity, 95% identity, 98% identity, 99% identity, or even 100% identity to the protein set forth in SEQ ID NO:1. The particle can be a particle comprising another AAV and AAV2 capsid protein, i.e., a chimeric protein. Variations in the amino acid sequence of the AAV2 capsid protein are contemplated herein, as long as the resulting viral particle comprising the AAV2 capsid remains antigenically or immunologically distinct from AAV4, as can be routinely determined by standard methods. Specifically, for example, ELISA and Western blots can be used to determine whether a viral particle is antigenically or immunologically distinct from AAV4. Furthermore, the AAV2 viral particle preferably retains tissue tropism distinction from AAV4, such as that exemplified in the examples herein, though an AAV2 chimeric particle comprising at least one AAV2 coat protein may have a different tissue tropism from that of an AAV2 particle consisting only of AAV2 coat proteins.

As indicated in FIGS. 1A and 1B, AAV2 capsid sequence and AAV4 capsid sequence are about 60% homologous. In certain embodiments, the AAV2 capsid comprises (or consists of) a sequence that is at least 65% homologous to the amino acid sequence set forth in SEQ ID NO:1.

In certain embodiments, the invention further provides an AAV2 particle containing, i.e., encapsidating, a vector comprising a pair of AAV2 inverted terminal repeats. The nucleotide sequence of AAV2 ITRs is known in the art. Furthermore, the particle can be a particle comprising both AAV4 and AAV2 capsid proteins, i.e., a chimeric protein. Moreover, the particle can be a particle encapsidating a vector comprising a pair of AAV inverted terminal repeats from other AAVs (e.g., AAV1-AAV9 and AAVrh10). The vector encapsidated in the particle can further comprise an exogenous nucleic acid inserted between the inverted terminal repeats.

The following features of AAV have made it an attractive vector for gene transfer. AAV vectors have been shown in vitro to stably integrate into the cellular genome; possess a broad host range; transduce both dividing and non dividing cells in vitro and in vivo and maintain high levels of expression of the transduced genes. Viral particles are heat stable, resistant to solvents, detergents, changes in pH, temperature, and can be concentrated on CsCl gradients or by other means. The present invention provides methods of administering AAV particles, recombinant AAV vectors, and recombinant AAV virions. For example, an AAV2 particle is a viral particle comprising an AAV2 capsid protein, or an AAV4 particle is a viral particle comprising an AAV4 capsid protein. A recombinant AAV2 vector is a nucleic acid construct that comprises at least one unique nucleic acid of AAV2. A recombinant AAV2 virion is a particle containing a recombinant AAV2 vector. To be considered within the term "AAV2 ITRs" the nucleotide sequence must retain one or both features described herein that distinguish the AAV2 ITR from the AAV4 ITR: (1) three (rather than four as in AAV4) "GAGC" repeats and (2) in the AAV2 ITR Rep binding site the fourth nucleotide in the first two "GAGC" repeats is a C rather than a T.

The promoter to drive expression of the protein or the sequence encoding another agent to be delivered can be any desired promoter, selected by known considerations, such as the level of expression of a nucleic acid functionally linked to the promoter and the cell type in which the vector is to be used. Promoters can be an exogenous or an endogenous promoter. Promoters can include, for example, known strong promoters such as SV40 or the inducible metallothionein promoter, or an AAV promoter, such as an AAV p5 promoter. Additional examples of promoters include promoters derived from actin genes, immunoglobulin genes, cytomegalovirus (CMV), adenovirus, bovine papilloma virus, adenoviral promoters, such as the adenoviral major late promoter, an inducible heat shock promoter, respiratory syncytial virus, Rous sarcomas virus (RSV), etc.

The AAV vector can further comprise an exogenous (heterologous) nucleic acid functionally linked to the promoter. By "heterologous nucleic acid" is meant that any heterologous or exogenous nucleic acid can be inserted into the vector for transfer into a cell, tissue or organism. The nucleic acid can encode a polypeptide or protein or an antisense RNA, for example. By "functionally linked" is meant such that the promoter can promote expression of the heterologous nucleic acid, as is known in the art, such as appropriate orientation of the promoter relative to the heterologous nucleic acid. Furthermore, the heterologous nucleic acid preferably has all appropriate sequences for expression of the nucleic acid, as known in the art, to functionally encode, i.e., allow the nucleic acid to be expressed. The nucleic acid can include, for example, expression control sequences, such as an enhancer, and necessary information processing sites, such as ribosome binding sites, RNA splice sites, polyadenylation sites, and transcriptional terminator sequences. The nucleic acid can encode more than one gene product, limited only by the size of nucleic acid that can be packaged.

The heterologous nucleic acid can encode beneficial proteins that replace missing or defective proteins required by the subject into which the vector in transferred or can encode a cytotoxic polypeptide that can be directed, e.g., to cancer cells or other cells whose death would be beneficial to the subject. The heterologous nucleic acid can also encode antisense RNAs that can bind to, and thereby inactivate, mRNAs made by the subject that encode harmful proteins. In one embodiment, antisense polynucleotides can be produced from a heterologous expression cassette in an AAV viral construct where the expression cassette contains a sequence that promotes cell-type specific expression.

Examples of heterologous nucleic acids which can be administered to a cell or subject as part of the present AAV vector can include, but are not limited to the nucleic acids encoding therapeutic agents, such as lysosomal hydrolases; tumor necrosis factors (TNF), such as TNF-alpha; interferons, such as interferon-alpha, interferon-beta, and interferon-gamma; interleukins, such as IL-1, IL-1beta, and ILs-2 through -14; GM-CSF; adenosine deaminase; secreted factors such as growth factors; ion channels; chemotherapeutics; lysosomal proteins; anti-apoptotic gene products; proteins promoting neural survival such as glutamate receptors and growth factors; cellular growth factors, such as lymphokines; soluble CD4; Factor VIII; Factor IX; T-cell receptors; LDL receptor; ApoE; ApoC; alpha-1 antitrypsin; ornithine transcarbamylase (OTC); cystic fibrosis transmembrane receptor (CFTR); insulin; Fc receptors for antigen binding domains of antibodies, such as immunoglobulins; and antisense sequences which inhibit viral replication, such as antisense sequences which inhibit replication of hepatitis B or hepatitis non-A, non-B virus. Furthermore, the nucleic acid can encode more than one gene product, limited only by the size of nucleic acid that can be packaged.

An AAV2 particle is a viral particle comprising an AAV2 capsid protein. Variations in the amino acid sequence of the AAV2 capsid protein are contemplated herein, as long as the resulting viral particle comprising the AAV2 capsid remains antigenically or immunologically distinct from AAV4, as can be routinely determined by standard methods. Specifically, for example, ELISA and Western blots can be used to determine whether a viral particle is antigenically or immunologically distinct from other AAV serotypes.

The term "polypeptide" as used herein refers to a polymer of amino acids and includes full-length proteins and fragments thereof. Thus, "protein" and "polypeptide" are often used interchangeably herein. Substitutions can be selected by known parameters to be neutral. As will be appreciated by those skilled in the art, the invention also includes those polypeptides having slight variations in amino acid sequences or other properties. Such variations may arise naturally as allelic variations (e.g. due to genetic polymorphism) or may be produced by human intervention (e.g., by mutagenesis of cloned DNA sequences), such as induced point, deletion, insertion and substitution mutants. Minor changes in amino acid sequence are generally preferred, such as conservative amino acid replacements, small internal deletions or insertions, and additions or deletions at the ends of the molecules. These modifications can result in changes in the amino acid sequence, provide silent mutations, modify a restriction site, or provide other specific mutations.

The present method provides a method of delivering a nucleic acid to a cell comprising administering to the cell an AAV particle containing a vector comprising the nucleic acid inserted between a pair of AAV inverted terminal repeats, thereby delivering the nucleic acid to the cell. Administration to the cell can be accomplished by any means, including simply contacting the particle, optionally contained in a desired liquid such as tissue culture medium, or a buffered saline solution, with the cells. The particle can be allowed to remain in contact with the cells for any desired length of time, and typically the particle is administered and allowed to remain indefinitely. For such in vitro methods, the virus can be administered to the cell by standard viral transduction methods, as known in the art and as exemplified herein. Titers of virus to administer can vary, particularly depending upon the cell type, but will be typical of that used for AAV transduction in general. Additionally the titers used to transduce the particular cells in the present examples can be utilized. The cells can include any desired cell in humans as well as other large (non-rodent) mammals, such as primates, horse, sheep, goat, pig, and dog.

More specifically, the present invention provides a method of delivering a nucleic acid to a cell with contact to the circulating CSF, such as an ependymal cell, a pial cell, meningeal cell, a brain endothelial cell, comprising administering to the cell an AAV particle containing a vector comprising the nucleic acid inserted between a pair of AAV inverted terminal repeats, thereby delivering the nucleic acid to the cell.

The present invention further provides a method of delivering a nucleic acid to a cell in a subject comprising administering to the subject an AAV particle comprising the nucleic acid inserted between a pair of AAV inverted terminal repeats, thereby delivering the nucleic acid to a cell in the subject.

Also provided is a method of delivering a nucleic acid to an ependymal, pial or other meningeal cell in a subject comprising administering to the subject an AAV particle comprising the nucleic acid inserted between a pair of AAV inverted terminal repeats, thereby delivering the nucleic acid to the ependymal, pial or other meningeal cell in the subject.

In certain embodiments, the amino acid sequence that targets brain vascular endothelium targets brain vascular endothelium in a subject that has a disease, e.g., a lysosomal storage disease.

In certain embodiments, the amino acid sequence that targets brain vascular endothelium targets brain vascular endothelium in a subject that does not have a lysosomal storage disease.

In certain embodiments, the viral vector comprises a nucleic acid sequence encoding a therapeutic agent. In certain embodiments, the therapeutic agent is TPP1.

Certain embodiments of the present disclosure provide a cell comprising a viral vector as described herein.

Certain embodiments of the present disclosure provide a method of treating a disease in a mammal comprising administering a viral vector or the cell as described herein to the mammal.

In certain embodiments, the mammal is human.

In certain embodiments, the disease is a lysosomal storage disease (LSD). In certain embodiments, the LSD is infantile or late infantile ceroid lipofuscinoses, Gaucher, Juvenile Batten, Fabry, MLD, Sanfilippo A, Late Infantile Batten, Hunter, Krabbe, Morquio, Pompe, Niemann-Pick C, Tay-Sachs, Hurler (MPS-I H), Sanfilippo B, Maroteaux-Lamy, Niemann-Pick A, Cystinosis, Hurler-Scheie (MPS-I H/S), Sly Syndrome (MPS VII), Scheie (MPS-I S), Infantile Batten, GM1 Gangliosidosis, Mucolipidosis type or Sandhoff disease.

In certain embodiments, the disease is a neurodegenerative disease. In certain embodiments, the neurodegenerative disease is Alzheimer's disease, Huntington's disease, ALS, hereditary spastic hemiplegia, primary lateral sclerosis, spinal muscular atrophy, Kennedy's disease, a polyglutamine repeat disease, or Parkinson's disease.

Certain embodiments of the present disclosure provide a method to deliver an agent to the central nervous system of a subject, comprising administering to the CSF with a viral vector described herein so that the transduced ependymal, pial, endothelial and/or other meningeal cells express the therapeutic agent and deliver the agent to the central nervous system of the subject. In certain embodiments, the viral vector transduces ependymal, pial, endothelial and/or other meningeal cells.

Certain embodiments of the present disclosure provide a viral vector or cell as described herein for use in medical treatments.

Certain embodiments of the present disclosure provide a use of a viral vector or cell as described herein to prepare a medicament useful for treating a disease, e.g., a lysosomal storage disease, in a mammal.

The vector may further comprise a lysosomal enzyme (e.g., a lysosomal hydrolase), a secreted protein, a nuclear protein, or a cytoplasmic protein. As used herein, the term "secreted protein" includes any secreted protein, whether naturally secreted or modified to contain a signal sequence so that it can be secreted.

Certain embodiments of the present disclosure provide a use of a viral vector or cell as described herein to prepare a medicament useful for treating a disease, e.g., Alzheimer's disease, in a mammal.

The vector may further comprise a protective ApoE isoform protein. As used herein, the term "secreted protein" includes any secreted protein, whether naturally secreted or modified to contain a signal sequence so that it can be secreted. Nucleic acid is "operably linked" when it is placed into a functional relationship with another nucleic acid sequence. Generally, "operably linked" means that the DNA sequences being linked are contiguous. However, enhancers do not have to be contiguous. Linking is accomplished by ligation at convenient restriction sites. If such sites do not exist, the synthetic oligonucleotide adaptors or linkers are used in accordance with conventional practice. Additionally, multiple copies of the nucleic acid encoding enzymes may be linked together in the expression vector. Such multiple nucleic acids may be separated by linkers.

The present disclosure also provides a mammalian cell containing a vector described herein. The cell may be human, and may be from brain. The cell type may be a stem or progenitor cell population.

The present disclosure provides a method of treating a disease such as a genetic disease or cancer in a mammal by administering a polynucleotide, polypeptide, expression vector, or cell described herein. The genetic disease or cancer may be a lysosomal storage disease (LSD) such as infantile or late infantile ceroid lipofuscinoses, Gaucher, Juvenile Batten, Fabry, MLD, Sanfilippo A, Late Infantile Batten, Hunter, Krabbe, Morquio, Pompe, Niemann-Pick C, Tay-Sachs, Hurler (MPS-I H), Sanfilippo B, Maroteaux-Lamy, Niemann-Pick A, Cystinosis, Hurler-Scheie (MPS-I H/S), Sly Syndrome (MPS VII), Scheie (MPS-I S), Infantile Batten, GM1 Gangliosidosis, Mucolipidosis type II/III, or Sandhoff disease.

The genetic disease may be a neurodegenerative disease, such as Huntington's disease, ALS, hereditary spastic hemiplegia, primary lateral sclerosis, spinal muscular atrophy, Kennedy's disease, Alzheimer's disease, a polyglutamine repeat disease, or focal exposure such as Parkinson's disease.

Certain aspects of the disclosure relate to polynucleotides, polypeptides, vectors, and genetically engineered cells (modified in vivo), and the use of them. In particular, the disclosure relates to a method for gene or protein therapy that is capable of both systemic delivery of a therapeutically effective dose of the therapeutic agent.

According to one aspect, a cell expression system for expressing a therapeutic agent in a mammalian recipient is provided. The expression system (also referred to herein as a "genetically modified cell") comprises a cell and an expression vector for expressing the therapeutic agent. Expression vectors include, but are not limited to, viruses, plasmids, and other vehicles for delivering heterologous genetic material to cells. Accordingly, the term "expression vector" as used herein refers to a vehicle for delivering heterologous genetic material to a cell. In particular, the expression vector is a recombinant adenoviral, adeno-associated virus, or lentivirus or retrovirus vector.

The expression vector further includes a promoter for controlling transcription of the heterologous gene. The promoter may be an inducible promoter (described below). The expression system is suitable for administration to the mammalian recipient. The expression system may comprise a plurality of non-immortalized genetically modified cells, each cell containing at least one recombinant gene encoding at least one therapeutic agent.

The cell expression system is formed in vivo. According to yet another aspect, a method for treating a mammalian recipient in vivo is provided. The method includes introducing an expression vector for expressing a heterologous gene product into a cell of the patient in situ, such as via intravenous administration. To form the expression system in vivo, an expression vector for expressing the therapeutic agent is introduced in vivo into the mammalian recipient i.v., where the vector migrates via the vasculature to the brain.

According to yet another aspect, a method for treating a mammalian recipient in vivo is provided. The method includes introducing the target protein into the patient in vivo.

The expression vector for expressing the heterologous gene may include an inducible promoter for controlling transcription of the heterologous gene product. Accordingly, delivery of the therapeutic agent in situ is controlled by exposing the cell in situ to conditions, which induce transcription of the heterologous gene.

The mammalian recipient may have a condition that is amenable to gene replacement therapy. As used herein, "gene replacement therapy" refers to administration to the recipient of exogenous genetic material encoding a therapeutic agent and subsequent expression of the administered genetic material in situ. Thus, the phrase "condition amenable to gene replacement therapy" embraces conditions such as genetic diseases (i.e., a disease condition that is attributable to one or more gene defects), acquired pathologies (i.e., a pathological condition which is not attributable to an inborn defect), cancers and prophylactic processes (i.e., prevention of a disease or of an undesired medical condition). Accordingly, as used herein, the term "therapeutic agent" refers to any agent or material, which has a beneficial effect on the mammalian recipient. Thus, "therapeutic agent" embraces both therapeutic and prophylactic molecules having nucleic acid or protein components.

According to one embodiment, the mammalian recipient has a genetic disease and the exogenous genetic material comprises a heterologous gene encoding a therapeutic agent for treating the disease. In yet another embodiment, the mammalian recipient has an acquired pathology and the exogenous genetic material comprises a heterologous gene encoding a therapeutic agent for treating the pathology. According to another embodiment, the patient has a cancer and the exogenous genetic material comprises a heterologous gene encoding an anti-neoplastic agent. In yet another embodiment the patient has an undesired medical condition and the exogenous genetic material comprises a heterologous gene encoding a therapeutic agent for treating the condition.

As used herein, the terms "a protective ApoE isoform," "lysosomal enzyme," a "secreted protein," a "nuclear protein," or a "cytoplasmic protein" include variants or biologically active or inactive fragments of these polypeptides. A "variant" of one of the polypeptides is a polypeptide that is not completely identical to a native protein. Such variant protein can be obtained by altering the amino acid sequence by insertion, deletion or substitution of one or more amino acid. The amino acid sequence of the protein is modified, for example by substitution, to create a polypeptide having substantially the same or improved qualities as compared to the native polypeptide. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spacial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains.

The amino acid changes are achieved by changing the codons of the corresponding nucleic acid sequence. It is known that such polypeptides can be obtained based on substituting certain amino acids for other amino acids in the polypeptide structure in order to modify or improve biological activity. For example, through substitution of alternative amino acids, small conformational changes may be conferred upon a polypeptide that results in increased activity. Alternatively, amino acid substitutions in certain polypeptides may be used to provide residues, which may then be linked to other molecules to provide peptide-molecule conjugates which, retain sufficient properties of the starting polypeptide to be useful for other purposes.

One can use the hydropathic index of amino acids in conferring interactive biological function on a polypeptide, wherein it is found that certain amino acids may be substituted for other amino acids having similar hydropathic indices and still retain a similar biological activity. Alternatively, substitution of like amino acids may be made on the basis of hydrophilicity, particularly where the biological function desired in the polypeptide to be generated in intended for use in immunological embodiments. The greatest local average hydrophilicity of a "protein", as governed by the hydrophilicity of its adjacent amino acids, correlates with its immunogenicity. Accordingly, it is noted that substitutions can be made based on the hydrophilicity assigned to each amino acid.

In using either the hydrophilicity index or hydropathic index, which assigns values to each amino acid, it is preferred to conduct substitutions of amino acids where these values are ±2, with ±1 being particularly preferred, and those with in ±0.5 being the most preferred substitutions.

The variant protein has at least 50%, at least about 80%, or even at least about 90% but less than 100%, contiguous amino acid sequence homology or identity to the amino acid sequence of a corresponding native protein.

The amino acid sequence of the variant polypeptide corresponds essentially to the native polypeptide's amino acid sequence. As used herein "correspond essentially to" refers to a polypeptide sequence that will elicit a biological response substantially the same as the response generated by the native protein. Such a response may be at least 60% of the level generated by the native protein, and may even be at least 80% of the level generated by native protein.

A variant may include amino acid residues not present in the corresponding native protein or deletions relative to the corresponding native protein. A variant may also be a truncated "fragment" as compared to the corresponding native protein, i.e., only a portion of a full-length protein. Protein variants also include peptides having at least one D-amino acid.

The variant protein may be expressed from an isolated DNA sequence encoding the variant protein. "Recombinant" is defined as a peptide or nucleic acid produced by the processes of genetic engineering. It should be noted that it is well-known in the art that, due to the redundancy in the genetic code, individual nucleotides can be readily exchanged in a codon, and still result in an identical amino acid sequence.

The present disclosure provides methods of treating a disease in a mammal by administering an expression vector to a cell or patient. For the gene therapy methods, a person having ordinary skill in the art of molecular biology and gene therapy would be able to determine, without undue experimentation, the appropriate dosages and routes of administration of the expression vector used in the novel methods of the present disclosure.

According to one embodiment, the cells are transformed or otherwise genetically modified in vivo. The cells from the mammalian recipient are transformed (i.e., transduced or transfected) in vivo with a vector containing exogenous genetic material for expressing a heterologous (e.g., recombinant) gene encoding a therapeutic agent and the therapeutic agent is delivered in situ.

As used herein, "exogenous genetic material" refers to a nucleic acid or an oligonucleotide, either natural or synthetic, that is not naturally found in the cells; or if it is naturally found in the cells, it is not transcribed or expressed at biologically significant levels by the cells. Thus, "exogenous genetic material" includes, for example, a non-naturally occurring nucleic acid that can be transcribed into anti-sense RNA, as well as a "heterologous gene" (i.e., a gene encoding a protein which is not expressed or is expressed at biologically insignificant levels in a naturally-occurring cell of the same type).

In the certain embodiments, the mammalian recipient has a condition that is amenable to gene replacement therapy. As used herein, "gene replacement therapy" refers to administration to the recipient of exogenous genetic material encoding a therapeutic agent and subsequent expression of the administered genetic material in situ. Thus, the phrase "condition amenable to gene replacement therapy" embraces conditions such as genetic diseases (i.e., a disease condition that is attributable to one or more gene defects), acquired pathologies (i.e., a pathological condition which is not attributable to an inborn defect), cancers and prophylactic processes (i.e., prevention of a disease or of an undesired medical condition). Accordingly, as used herein, the term "therapeutic agent" refers to any agent or material, which has a beneficial effect on the mammalian recipient. Thus, "therapeutic agent" embraces both therapeutic and prophylactic molecules having nucleic acid (e.g., antisense RNA) and/or protein components.

Alternatively, the condition amenable to gene replacement therapy is a prophylactic process, i.e., a process for preventing disease or an undesired medical condition. Thus, the instant disclosure embraces a cell expression system for delivering a therapeutic agent that has a prophylactic function (i.e., a prophylactic agent) to the mammalian recipient.

In summary, the term "therapeutic agent" includes, but is not limited to, agents associated with the conditions listed above, as well as their functional equivalents. As used herein, the term "functional equivalent" refers to a molecule (e.g., a peptide or protein) that has the same or an improved beneficial effect on the mammalian recipient as the therapeutic agent of which is it deemed a functional equivalent.

The above-disclosed therapeutic agents and conditions amenable to gene replacement therapy are merely illustrative and are not intended to limit the scope of the instant disclosure. The selection of a suitable therapeutic agent for treating a known condition is deemed to be within the scope of one of ordinary skill of the art without undue experimentation.

AAV Vectors

In one embodiment, a viral vector of the disclosure is an AAV vector. An "AAV" vector refers to an adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are eight known serotypes of primate AAVs, AAV-1 to AAV-9 and AAVrh10. For example, serotype AAV2 is used to refer to an AAV which contains capsid proteins encoded from the cap gene of AAV2 and a genome containing 5' and 3' ITR sequences from the same AAV2 serotype. As used herein, for example, rAAV1 may be used to refer an AAV having both capsid proteins and 5'-3' ITRs from the same serotype or it may refer to an AAV having capsid proteins from one serotype and 5'-3' ITRs from a different AAV serotype, e.g., capsid from AAV serotype 2 and ITRs from AAV serotype 5. For each example illustrated herein the description of the vector design and production describes the serotype of the capsid and 5'-3' ITR sequences. The abbreviation "rAAV" refers to recombinant adeno-associated virus, also referred to as a recombinant AAV vector (or "rAAV vector").

An "AAV virus" or "AAV viral particle" refers to a viral particle composed of at least one AAV capsid protein (preferably by all of the capsid proteins of a wild-type AAV) and an encapsidated polynucleotide. If the particle comprises heterologous polynucleotide (i.e., a polynucleotide other than a wild-type AAV genome such as a transgene to be delivered to a mammalian cell), it is typically referred to as "rAAV".

In one embodiment, the AAV expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is flanked (5' and 3') with functional AAV ITR sequences.

By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV1, AAV2, AAV3, AAV4, AAV5, AAV7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

In one embodiment, AAV ITRs can be derived from any of several AAV serotypes, including without limitation, AAV1, AAV2, AAV3, AAV4, AAV5, AAV7, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

In one embodiment, AAV capsids can be derived from AAV2. Suitable DNA molecules for use in AAV vectors will be less than about 5 kilobases (kb), less than about 4.5 kb, less than about 4 kb, less than about 3.5 kb, less than about 3 kb, less than about 2.5 kb in size and are known in the art.

In one embodiment, the selected nucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, pol II promoters, pol III promoters, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

In one embodiment, both heterologous promoters and other control elements, such as CNS-specific and inducible promoters, enhancers and the like, will be of particular use. Examples of heterologous promoters include the CMV promoter. Examples of CNS-specific promoters include those isolated from the genes from myelin basic protein (MBP), glial fibrillary acid protein (GFAP), and neuron specific enolase (NSE). Examples of inducible promoters include DNA responsive elements for ecdysone, tetracycline, hypoxia and aufin.

In one embodiment, the AAV expression vector which harbors the DNA molecule of interest bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art.

Alternatively, AAV ITRs can be excised from the viral genome or from an AAV vector containing the same and fused 5' and 3' of a selected nucleic acid construct that is present in another vector using standard ligation techniques. For example, ligations can be accomplished in 20 mM Tris-Cl pH 7.5, 10 mM $MgCl_2$, 10 mM DTT, 33 μg/ml BSA, 10 mM-50 mM NaCl, and either 40 uM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 μg/ml total DNA concentrations (5-100 nM total end concentration). AAV vectors which contain ITRs.

Additionally, chimeric genes can be produced synthetically to include AAV ITR sequences arranged 5' and 3' of one or more selected nucleic acid sequences. Preferred codons for expression of the chimeric gene sequence in mammalian CNS cells can be used. The complete chimeric sequence is assembled from overlapping oligonucleotides prepared by standard methods.

In order to produce rAAV virions, an AAV expression vector is introduced into a suitable host cell using known techniques, such as by transfection. A number of transfection techniques are generally known in the art. See, e.g., Sambrook et al. (1989) Molecular Cloning, a laboratory manual, Cold Spring Harbor Laboratories, New York. Particularly suitable transfection methods include calcium phosphate co-precipitation, direct micro-injection into cultured cells, electroporation, liposome mediated gene transfer, lipid-mediated transduction, and nucleic acid delivery using high-velocity microprojectiles.

In one embodiment, suitable host cells for producing rAAV virions include microorganisms, yeast cells, insect cells, and mammalian cells, that can be, or have been, used as recipients of a heterologous DNA molecule. The term includes the progeny of the original cell which has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL1573) can be used in the practice of the present disclosure. Particularly, the human cell line 293 is a human embryonic kidney cell line that has been transformed with adenovirus type-5 DNA fragments, and expresses the adenoviral E1a and E1b genes. The 293 cell line is readily transfected, and provides a particularly convenient platform in which to produce rAAV virions.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. Suitable homologues of the AAV rep coding region include the human herpesvirus 6 (HHV-6) rep gene which is also known to mediate AAV-2 DNA replication.

By "AAV cap coding region" is meant the art-recognized region of the AAV genome which encodes the capsid proteins VP1, VP2, and VP3, or functional homologues thereof. These Cap expression products supply the packaging functions which are collectively required for packaging the viral genome.

In one embodiment, AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. A number of other vectors have been described which encode Rep and/or Cap expression products.

Methods of delivery of viral vectors include injecting the AAV2 into the CSF. Generally, rAAV virions may be introduced into cells of the CNS using either in vivo or in vitro transduction techniques. If transduced in vitro, the desired recipient cell will be removed from the subject, transduced with rAAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant AAV virions with CNS cells e.g., in appropriate media, and screening for those cells harboring the DNA of interest can be screened using conventional techniques such as Southern blots and/or PCR, or by using selectable markers. Transduced cells can then be formulated into pharmaceutical compositions, described more fully below, and the composition introduced into the subject by various techniques, such as by grafting, intramuscular, intravenous, subcutaneous and intraperitoneal injection.

In one embodiment, pharmaceutical compositions will comprise sufficient genetic material to produce a therapeutically effective amount of the nucleic acid of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., N.J. 1991).

It should be understood that more than one transgene could be expressed by the delivered viral vector. Alternatively, separate vectors, each expressing one or more different transgenes, can also be delivered to the CNS as described herein. Furthermore, it is also intended that the viral vectors delivered by the methods of the present disclosure be combined with other suitable compositions and therapies.

As is apparent to those skilled in the art in view of the teachings of this specification, an effective amount of viral vector which must be added can be empirically determined. Administration can be effected in one dose, continuously or intermittently throughout the course of treatment. Methods of determining the most effective means and dosages of administration are well known to those of skill in the art and will vary with the viral vector, the composition of the therapy, the target cells, and the subject being treated. Single and multiple administrations can be carried out with the dose level and pattern being selected by the treating physician.

In certain embodiments, the rAAV is administered at a dose of about 1-5 ml of $1\times10^5$-$1\times10^{16}$ vg/ml. In certain embodiments, the rAAV is administered at a dose of about 1-3 ml of $1\times10^7$-$1\times10^{14}$ vg/ml. In certain embodiments, the rAAV is administered at a dose of about 1-2 ml of $1\times10^8$-$1\times10^{13}$ vg/ml.

Formulations containing the rAAV particles will contain an effective amount of the rAAV particles in a vehicle, the effective amount being readily determined by one skilled in the art. The rAAV particles may typically range from about 1% to about 95% (w/w) of the composition, or even higher or lower if appropriate. The quantity to be administered depends upon factors such as the age, weight and physical condition of the animal or the human subject considered for treatment. Effective dosages can be established by one of ordinary skill in the art through routine trials establishing dose response curves. The subject is treated by administration of the rAAV particles in one or more doses. Multiple doses may be administered as is required to maintain adequate enzyme activity.

Vehicles including water, aqueous saline, artificial CSF, or other known substances can be employed with the subject invention. To prepare a formulation, the purified composition can be isolated, lyophilized and stabilized. The composition may then be adjusted to an appropriate concentration, optionally combined with an anti-inflammatory agent, and packaged for use.

TPP1 Protein

In certain embodiments, the nucleic acid being administered encodes TPP1, a TPP1 that has substantial identity to wildtype TPP1, and/or a variant, mutant or fragment of TPP1. The human TPP1 amino acid sequence is provided in FIG. 14, and the nucleic acid sequence is provided in FIGS. 15A-15B. FIG. 16 provides the *Macaca mulatta* TPP1 amino acid sequence, and FIG. 17 provides the *Macaca fascicularis* TPP1 amino acid sequence. In certain embodiments, the TPP1 protein can have about 70% homology, about 75% homology, 80% homology, 85% homology, 90% homology, 95% homology, 98% homology, 99% homology, or even 100% homology to the protein set forth in FIG. 14, 16 or 17. The TPP1 protein can have about 70% identity, about 75% identity, 80% identity, 85% identity, 90% identity, 95% identity, 98% identity, 99% identity, or even 100% identity to the protein set forth in FIG. 14, 16 or 17.

A mutant protein refers to the protein encoded by a gene having a mutation, e.g., a missense or nonsense mutation in TPP1. The term "nucleic acid" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues.

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein. In certain embodiments, the fragment or portion is biologically functional (i.e., retains 5%, 10%, 15%, 20%, 25%, 30%, 35%, 40%, 45%, 50%, 55%, 60%, 65%, 70%, 75%, 80%, 85%, 90%, 95%, 99% or 100% of enzymatic activity of the wildtype TPP1).

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence. In certain embodiments, the variant is biologically functional (i.e., retains 5%, 10%, 15%, 20%, 25%, 30%, 35%, 40%, 45%, 50%, 55%, 60%, 65%, 70%, 75%, 80%, 85%, 90%, 95%, 99% or 100% of enzymatic activity of the wildtype TPP1).

"Conservatively modified variations" of a particular nucleic acid sequence refers to those nucleic acid sequences that encode identical or essentially identical amino acid sequences. Because of the degeneracy of the genetic code, a large number of functionally identical nucleic acids encode any given polypeptide. For instance, the codons CGT, CGC, CGA, CGG, AGA and AGG all encode the amino acid arginine Thus, at every position where an arginine is specified by a codon, the codon can be altered to any of the corresponding codons described without altering the encoded protein. Such nucleic acid variations are "silent variations," which are one species of "conservatively modified variations." Every nucleic acid sequence described herein that encodes a polypeptide also describes every possible silent variation, except where otherwise noted. One of skill in the art will recognize that each codon in a nucleic acid (except ATG, which is ordinarily the only codon for methionine) can be modified to yield a functionally identical molecule by standard techniques. Accordingly, each "silent variation" of a nucleic acid that encodes a polypeptide is implicit in each described sequence.

The term "substantial identity" of polynucleotide sequences means that a polynucleotide comprises a sequence that has at least 70%, 71%, 72%, 73%, 74%, 75%, 76%, 77%, 78%, or 79%, or at least 80%, 81%, 82%, 83%, 84%, 85%, 86%, 87%, 88%, or 89%, or at least 90%, 91%, 92%, 93%, or 94%, or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, or even at least 95%.

The term "substantial identity" in the context of a peptide indicates that a peptide comprises a sequence with at least 70%, 71%, 72%, 73%, 74%, 75%, 76%, 77%, 78%, or 79%, or 80%, 81%, 82%, 83%, 84%, 85%, 86%, 87%, 88%, or 89%, or at least 90%, 91%, 92%, 93%, or 94%, or even, 95%, 96%, 97%, 98% or 99%, sequence identity to the reference sequence over a specified comparison window. An indication that two peptide sequences are substantially identical is that one peptide is immunologically reactive with antibodies raised against the second peptide. Thus, a peptide is substantially identical to a second peptide, for example, where the two peptides differ only by a conservative substitution.

Apolipoprotein E (ApoE)

There are several different human apolipoprotein E (ApoE) isoforms, the presence of some of these isoforms in the brain increase the risk for Alzheimer's disease (AD), whereas the presence of other isoforms decreases the risk for AD. The presence of the ApoE ε4 isoform is a strong genetic risk factor for late-onset, sporadic AD. (Casellano et al., *Sci Transl Med,* 3(89):89ra57 (29 Jun. 2011).) The ApoE ε4 allele strongly increases AD risk and decreases age of onset. On the other hand, the presence of the ApoE ε2 allele appears to decrease AD risk. It is suggested that human ApoE isoforms differentially affect the clearance or synthesis of amyloid-β (Aβ) in vivo.

In certain embodiments, the nucleic acid being administered encodes ApoE, a ApoE that has substantial identity to wildtype ApoE, or a variant, mutant and/or or fragment of ApoE. In certain embodiments, the nucleic acid encodes ApoE ε2, an ApoE ε2 that has substantial identity to wildtype ApoE ε2, and/or a variant, mutant or fragment of ApoE ε2.

Immunesuppression Agents

In certain embodiments, an immunesuppression agent is also administered to the mammal. In certain embodiments, the immunesuppression agent is an anti-inflammatory agent. In certain embodiments, the anti-inflammatory agent is mycophenolate. In certain embodiments, the anti-inflammatory agent is administered prior to the administration of the rAAV particles. In certain embodiments, the anti-inflammatory agent is administered concurrently to the administration of the rAAV particles. In certain embodiments, the anti-inflammatory agent is administered subsequent to the administration of the rAAV particles.

In certain embodiments, the anti-inflammatory agent is administered parenterally, such as by intramuscular or subcutaneous injection in an appropriate vehicle. Other modes of administration, however, such as oral, intranasal or intradermal delivery, are also acceptable. In certain embodiments, a composition comprising the rAAV particle and the anti-inflammatory agent is prepared and the anti-inflammatory agent and rAAV particle are administered simultaneously to the mammal's cisterna magna and/or to the mammal's brain ventricle, subarachnoid space and/or intrathecal space.

Methods for Introducing Genetic Material into Cells

The exogenous genetic material (e.g., a cDNA encoding one or more therapeutic proteins) is introduced into the cell in vivo by genetic transfer methods, such as transfection or transduction, to provide a genetically modified cell. Various expression vectors (i.e., vehicles for facilitating delivery of exogenous genetic material into a target cell) are known to one of ordinary skill in the art.

As used herein, "transfection of cells" refers to the acquisition by a cell of new genetic material by incorporation of added DNA. Thus, transfection refers to the insertion of nucleic acid into a cell using physical or chemical methods. Several transfection techniques are known to those of ordinary skill in the art including: calcium phosphate DNA co-precipitation; DEAE-dextran; electroporation; cationic liposome-mediated transfection; and tungsten particle-facilitated microparticle bombardment. Strontium phosphate DNA co-precipitation is another possible transfection method.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous genetic material contained within the retrovirus is incorporated into the genome of the transduced cell. A cell that has been transduced with a chimeric DNA virus (e.g., an adenovirus carrying a cDNA encoding a therapeutic agent), will not have the exogenous genetic material incorporated into its genome but will be capable of expressing the exogenous genetic material that is retained extrachromosomally within the cell.

Typically, the exogenous genetic material includes the heterologous gene (usually in the form of a cDNA comprising the exons coding for the therapeutic protein) together with a promoter to control transcription of the new gene. The promoter characteristically has a specific nucleotide sequence necessary to initiate transcription. Optionally, the exogenous genetic material further includes additional sequences (i.e., enhancers) required to obtain the desired gene transcription activity. For the purpose of this discussion an "enhancer" is simply any non-translated DNA sequence which works contiguous with the coding sequence (in cis) to change the basal transcription level dictated by the promoter. The exogenous genetic material may introduced into the cell genome immediately downstream from the promoter so that the promoter and coding sequence are operatively linked so as to permit transcription of the coding sequence. A retroviral expression vector may include an exogenous promoter element to control transcription of the inserted exogenous gene. Such exogenous promoters include both constitutive and inducible promoters.

Naturally-occurring constitutive promoters control the expression of essential cell functions. As a result, a gene under the control of a constitutive promoter is expressed under all conditions of cell growth. Exemplary constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the actin promoter, and other constitutive promoters known to those of skill in the art. In addition, many viral promoters function constitutively in eucaryotic cells. These include: the early and late promoters of SV40; the long terminal repeats (LTRs) of Moloney Leukemia Virus and other retroviruses; and the thymidine kinase promoter of Herpes Simplex Virus, among many others. Accordingly, any of the above-referenced constitutive promoters can be used to control transcription of a heterologous gene insert.

Genes that are under the control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of a therapeutic agent in the genetically modified cell. If the gene encoding the therapeutic agent is under the control of an inducible promoter, delivery of the therapeutic agent in situ is triggered by exposing the genetically modified cell in situ to conditions for permitting transcription of the therapeutic agent, e.g., by intraperitoneal injection of specific inducers of the inducible promoters which control transcription of the agent. For example, in situ expression by genetically modified cells of a therapeutic agent encoded by a gene under the control of the metallothionein promoter, is enhanced by contacting the genetically modified cells with a solution containing the appropriate (i.e., inducing) metal ions in situ.

Accordingly, the amount of therapeutic agent that is delivered in situ is regulated by controlling such factors as: (1) the nature of the promoter used to direct transcription of the inserted gene, (i.e., whether the promoter is constitutive or inducible, strong or weak); (2) the number of copies of the exogenous gene that are inserted into the cell; (3) the number of transduced/transfected cells that are administered (e.g., implanted) to the patient; (4) the size of the implant (e.g., graft or encapsulated expression system); (5) the number of implants; (6) the length of time the transduced/transfected cells or implants are left in place; and (7) the production rate of the therapeutic agent by the genetically modified cell. Selection and optimization of these factors for delivery of a therapeutically effective dose of a particular therapeutic agent is deemed to be within the scope of one of ordinary skill in the art without undue experimentation, taking into account the above-disclosed factors and the clinical profile of the patient.

In addition to at least one promoter and at least one heterologous nucleic acid encoding the therapeutic agent, the expression vector may include a selection gene, for example, a neomycin resistance gene, for facilitating selection of cells that have been transfected or transduced with the expression vector. Alternatively, the cells are transfected with two or more expression vectors, at least one vector containing the gene(s) encoding the therapeutic agent(s), the other vector containing a selection gene. The selection of a suitable promoter, enhancer, selection gene and/or signal sequence (described below) is deemed to be within the scope of one of ordinary skill in the art without undue experimentation.

The therapeutic agent can be targeted for delivery to an extracellular, intracellular or membrane location. If it is desirable for the gene product to be secreted from the cells, the expression vector is designed to include an appropriate secretion "signal" sequence for secreting the therapeutic gene product from the cell to the extracellular milieu. If it is desirable for the gene product to be retained within the cell, this secretion signal sequence is omitted. In a similar manner, the expression vector can be constructed to include "retention" signal sequences for anchoring the therapeutic agent within the cell plasma membrane. For example, all membrane proteins have hydrophobic transmembrane regions, which stop translocation of the protein in the membrane and do not allow the protein to be secreted. The construction of an expression vector including signal sequences for targeting a gene product to a particular location is deemed to be within the scope of one of ordinary skill in the art without the need for undue experimentation.

Example 1

Methods of Gene Transfer in Large Mammals

Lysosomal storage disorders (LSDs) constitute a large class of inherited metabolic disorders. Most LSDs are caused by lysosomal enzyme deficiencies which lead to organ damage and often central nervous system (CNS) degeneration. Late infantile neuronal ceroid lipofuscinosis (LINCL) is an autosomal recessive neurodegenerative disease caused by mutations in a ceroid-lipofuscinosis (CLN), neuronal 2 gene CLN2, which encodes the lysosomal protease tripeptidyl peptidase 1 (TPP1). LINCL is characterized clinically by normal birth and early development, onset of seizures by 18-24 months, progressive motor and cognitive decline, and premature death. The disease is due to a deficiency in TPP1, which is a soluble, M-6-P decorated lysosomal enzyme.

Enzyme-replacement therapy (ERT) is currently available for lysosomal storage diseases affecting peripheral tissues, but has not been used in patients with central nervous system (CNS) involvement. A recent study investigated whether enzyme delivery through the cerebrospinal fluid was a potential alternative route to the CNS for LINCL (Chang et al., *Molecular Therapy* 16:649-656, 2008). Treated mice showed attenuated neuropathology, and decreased resting tremor relative to vehicle-treated mice.

In the present work, it was investigated whether global delivery of a vector could be effectively performed in order to achieve steady-state levels of enzyme in the cerebrospinal fluid (CSF) by means of injection in the brain. Studies were performed in a dog model of LINCL. The LINCL dogs are normal at birth, but develop neurological signs around 7 months, testable cognitive deficits at ~5-6 months, seizures at 10-11 months, and progressive visual loss. The CLN2 gene mutation in the LINCL dog renders the TPP1 protein non-functional, and TPP1 protein is undetectable. With disease progression, brain tissues shrink, leading to enlarged ventricular spaces in the brain. Neurological symptoms include decline in balance and motor functions, loss of vision, tremors.

Affected LINCL pups were given gene therapy at three months of age. For gene therapy, AAV2-CLN2 generated (see WO 2012/135857), and was injected at a single site (lateral ventricle) or at two sites (lateral ventricle plus cisterna magna) in the brain. Needles were placed into the ventricle, or into the ventricle and cistern magna, and vector infused slowly over several minutes. While much of the TPP1 made within a cell stayed in that cell, a portion was secreted and taken up by neighboring cells. This property of secretion and uptake is called "cross-correction" (FIG. 2). Cross-correction is valuable in the context of gene therapy in that if the CLN2 gene is transferred to strategically situated cells in the LINCL brain, then this can allow for cross-correction of many surrounding cells.

Figure 3:
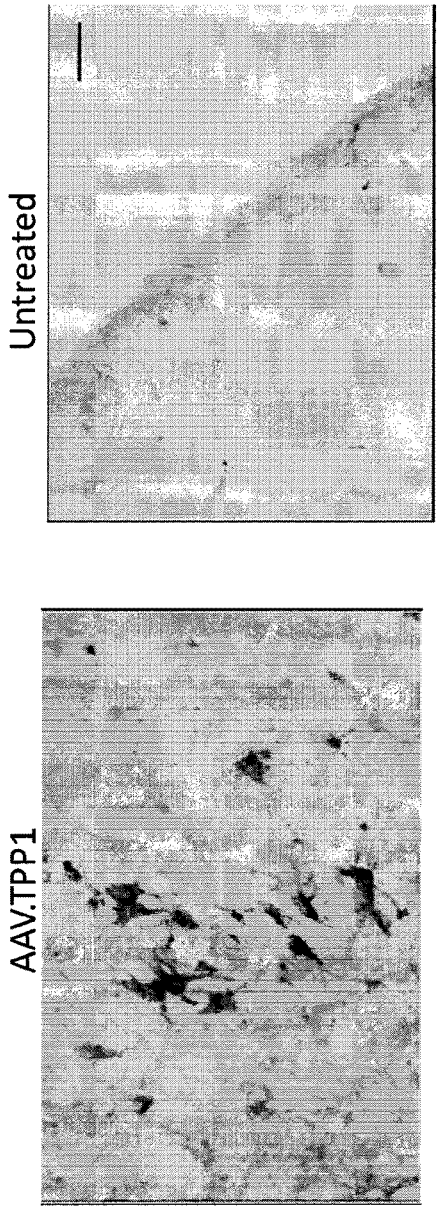
FIG. 3. Top: Immunohistochemical staining for human TPP1 after AAV2 mediated delivery into a LINCL dog model that is deficient in canine TPP1. Left, treated dog. Right, untreated deficient animal. Compare the strong positive staining on the left to the background staining in the right panel. Bottom. Western blot for TPP1 showing the presence of human TPP1 in the treated, deficient (LINCL) dog. Both normal and deficient dogs do not show the presence of the band, as they do not express human TPP1.
Figure 3:
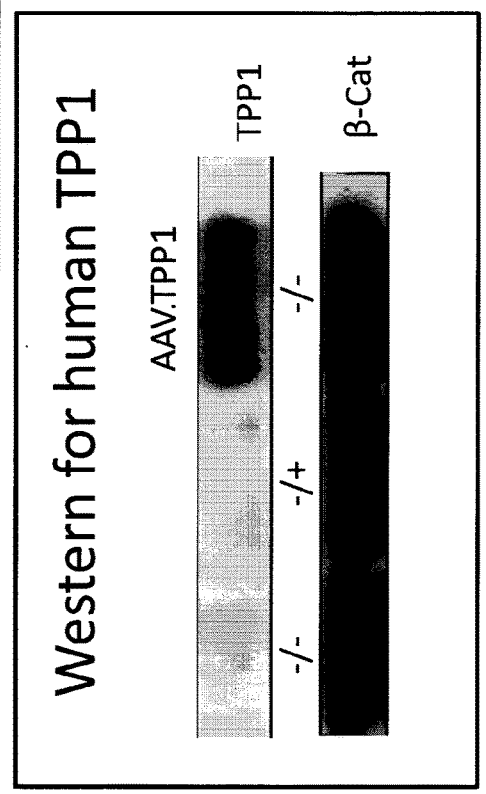
Figure 4A:
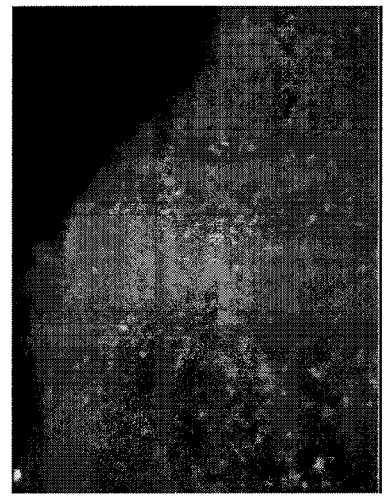
FIG. 4A. Microphotographs showing the representative autofluorescence depictive of the pathological accumulation of lipofuscin in the neuronal ceroid lipofuscinoses. Left panel, autofluorescence in an AAV2.TPP1 treated LINCL dog. Right panel, autofluoresence in a control, untreated LINCL dog. Note the reduction in autofluorence with therapy.
Figure 4A:
Figure 4B:
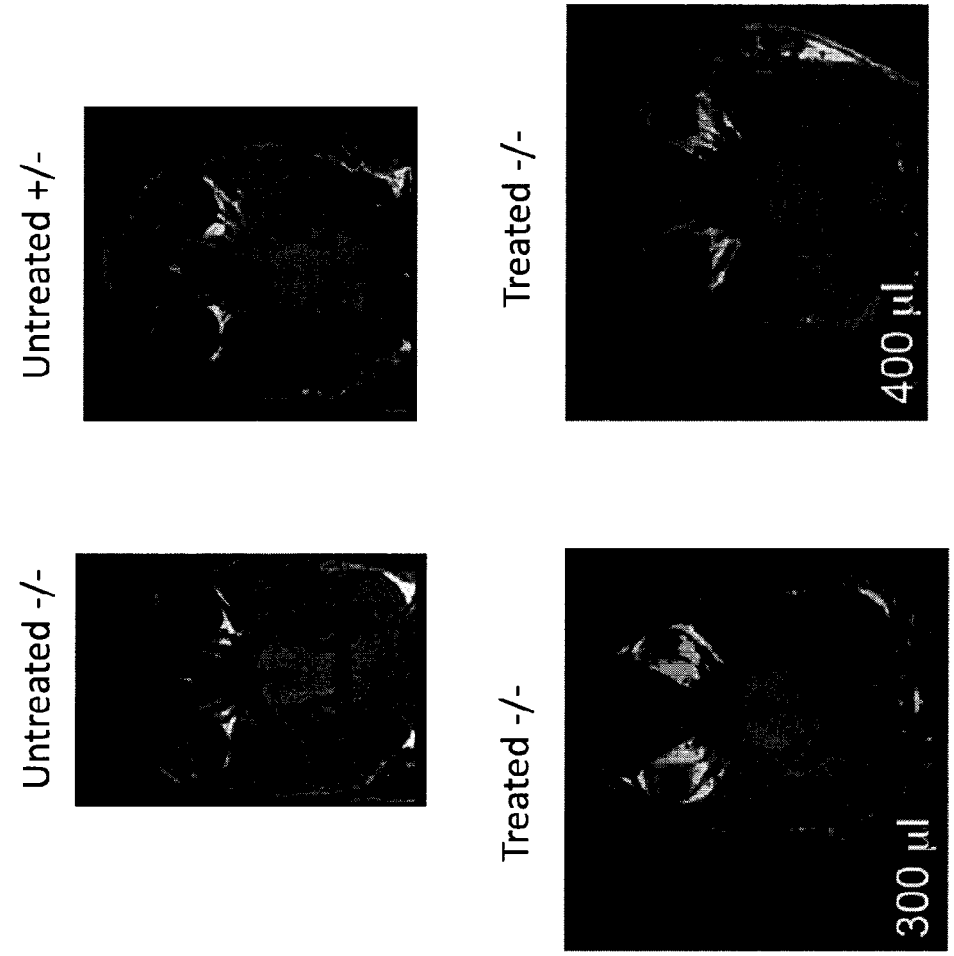
FIG. 4B. MRI scans of an untreated LINCL dog (upper left), a untreated normal dog (upper right), and two AAV.TPP1 treated dogs (lower panels). The volumes of vector delivered are indicated in the lower left of the bottom panels. The viral titer was approximately 1e13 genomes/mL.
Figure 4C:
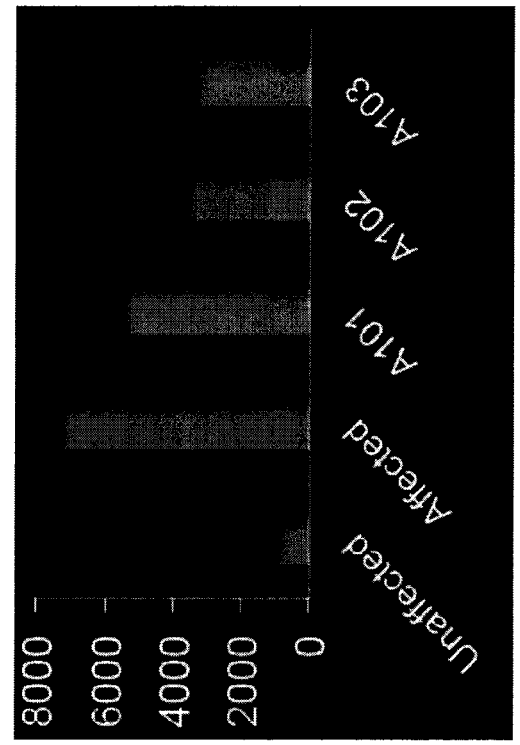
FIG. 4C. Volumetric reconstructions of the ventricles of the dogs imaged in 4B (left panels). The graph in the right panel denotes the volumes from the images in the left panels. Note the extensive reduction in ventricular volume even with these low doses of vector (stated in FIG. 4B legend).
Figure 4C:
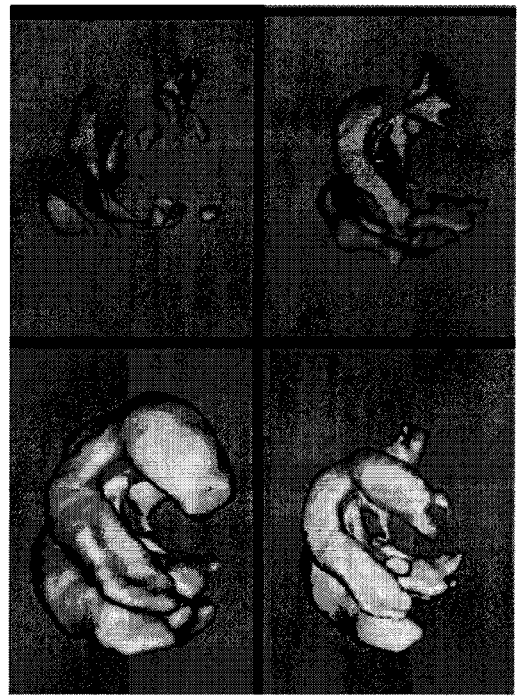
Figure 4D:
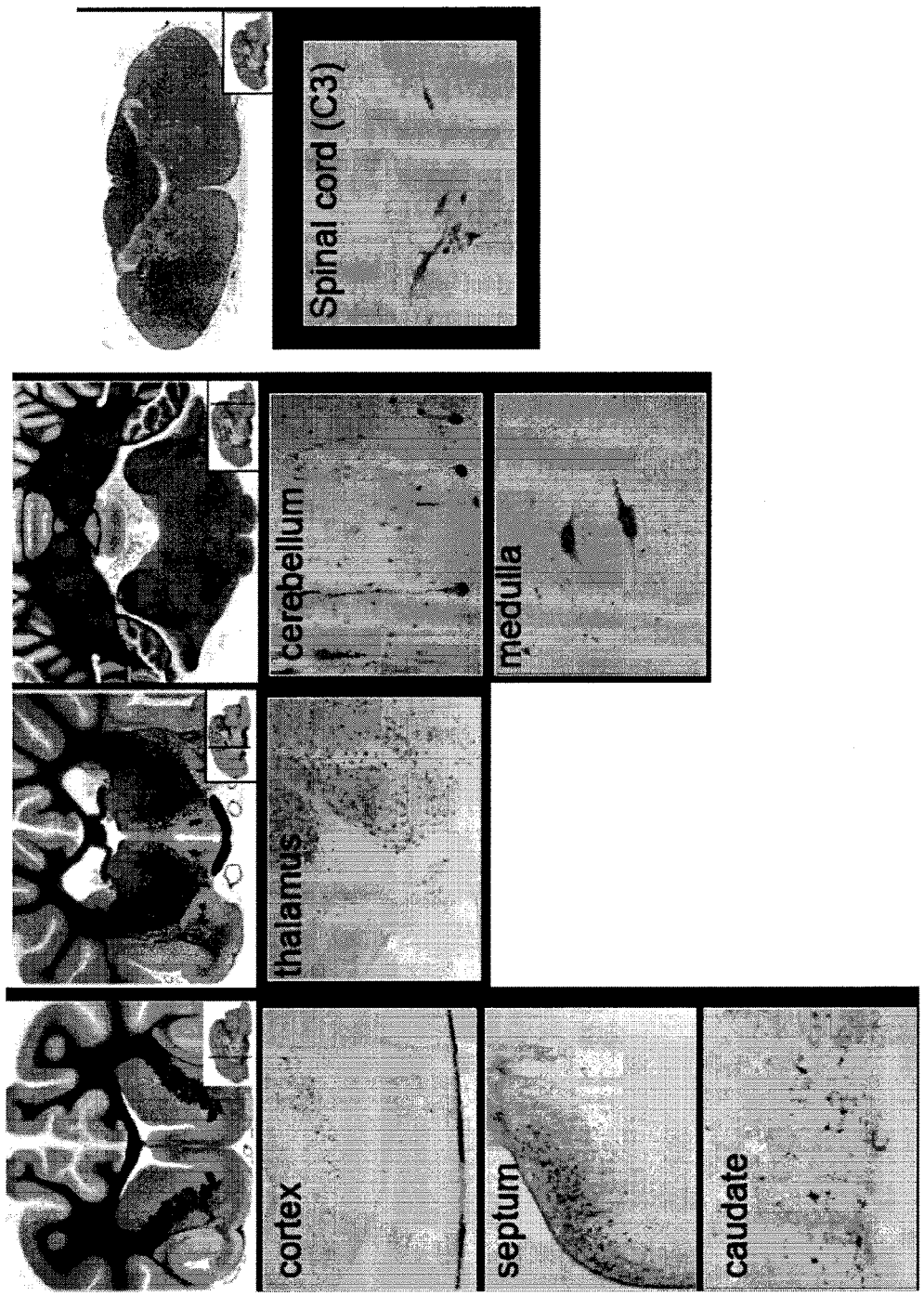
FIG. 4D. Immunohistochemical staining in varying brain regions shows extensive distribution of TPP1 protein after AAV.TPP1 gene transfer to the ventricular system of the LINCL dog. Top panels are coronal sections from the dog brain atlas; the lower right insets present the sagittal view of the coronal image. The immunohistochemically stained sections below the panels from the atlas show the extent of staining in sections from those regions. Together the data show extensive distribution of enzyme.

In the present study, the problem of globally delivering the therapeutic vector took advantage of the CSF flow in the brain by targeting cells that line the ventricles and cells that make up the meninges. AAV2-CLN2 was injected at a single site (lateral ventricle) or at two sites (lateral ventricle plus cisterna magna) in the brain. TPP1 expression was observed in Cln2$^{-/-}$ dogs after AAV delivery (FIG. 3). A significant positive impact was observed on ventricular volume. The effect of AAV.TPP1 on autofluorescence was also evaluated (FIG. 4A). FIG. 4B shows T1-MRI images of untreated and treated dogs. FIG. 4C shows the effects of AAV.TPP1 in LINCL dogs. FIG. 4D shows huTPP1 distribution after AAV2/2-huCLN2 administration.

In untreated affected dogs, ventricular spaces enlarge to ten times the size of normal dogs, whereas AAV2-CLN2 gene therapy significantly reduced this effect. Further, a broad distribution of enzyme was observed, as was a clinical benefit (lifespan and clinical examination). Without treatment, affected dogs show signs of disease in all 22 tests by 30 weeks of age. They reach end-stage disease and must be euthanized between 45 and 48 weeks of age. In dogs that received AAV2-CLN2 gene therapy, the onset of every one of these signs was delayed or prevented.

An increase in TPP1 activity was observed in CSF after combined cisterna and ventricular delivery.

Thus, in the LINCL dog, AAV2-CLN2 gene transfer resulted in TPP1 protein replenishment to many areas of the brain, and the results indicated that AAV2-CLN2 gene transfer provided significant therapeutic effects, reduced or delayed symptoms and improved the quality of life for the LINCL dogs.

Figure 5:
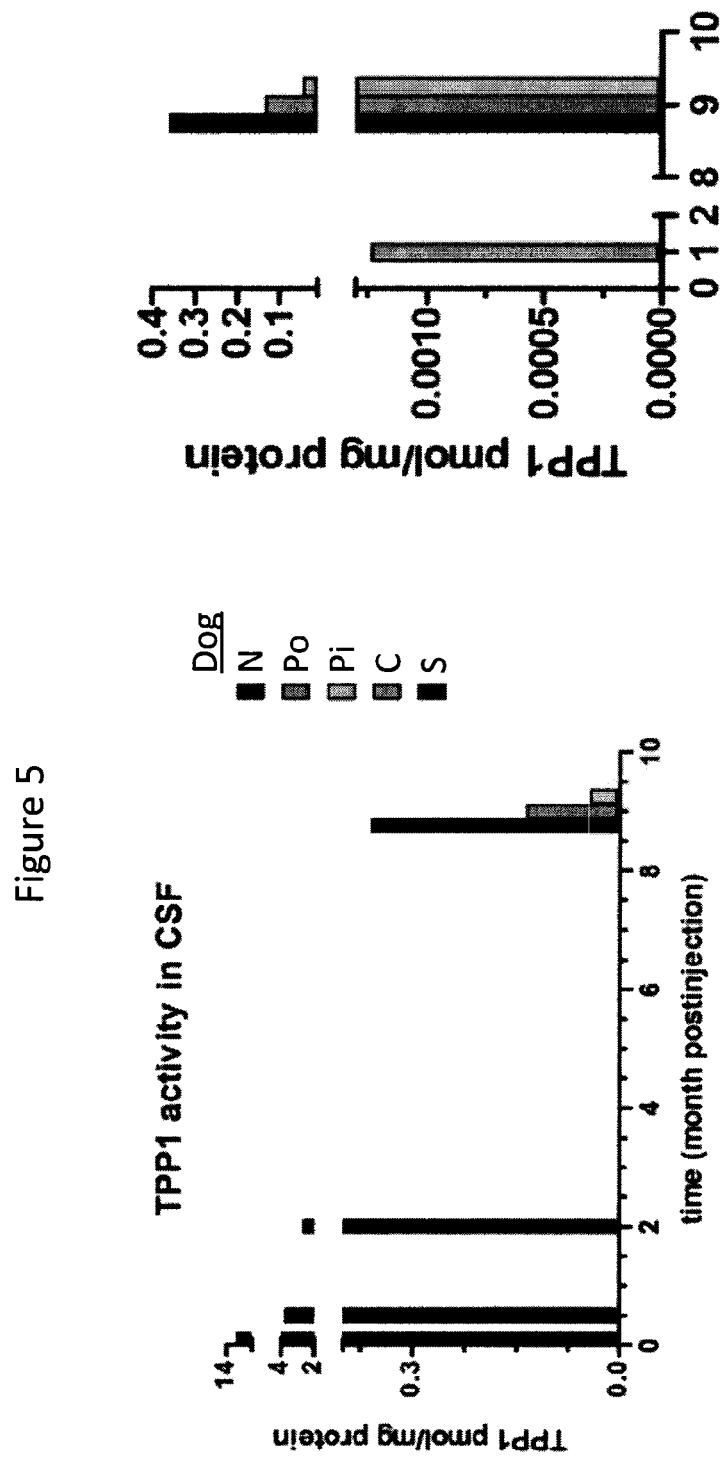
FIG. 5. huTPP1 enzyme activity in CSF following AAV.TPP1 delivery declined shortly after viral gene transfer. Left panel: TPP1 activity in CSF in treated Animals Co and S exceeds normal activity levels very soon after AAV.TPP1 gene transfer, and then rapidly declines to undetectable levels. Animals N, Po and Pi are normal or heterozygous dogs and are shown for reference only of the range of TPP1 activity levels in clinically normal dogs.
Figure 6:
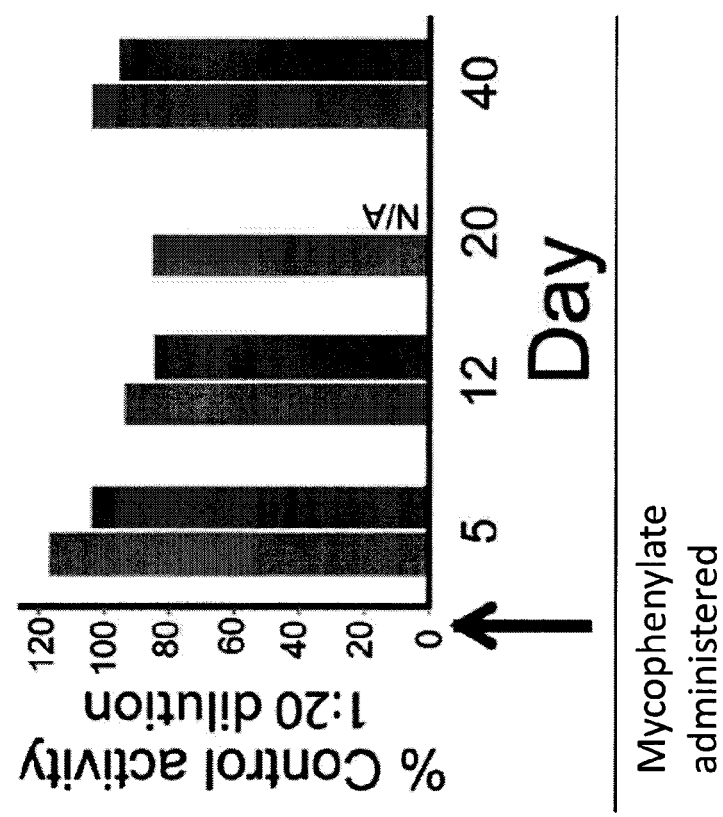
FIG. 6 shows the results of pre-treating with mycophenolate on providing for sustained activity.

The huTPP1 activity in CSF declined shortly after injection (FIG. 5). A broad distribution of enzyme was observed, but the levels were low at the time of sacrifice 6-8 months post-gene therapy. It was postulated that the decline in activity was a result of an immune response to the human enzyme in the dogs. In order to inhibit the decline in activity, an anti-inflammatory agent (mycophenolate) was introduced. The results indicated that the anti-inflammatory agent did not inhibit the enzymatic activity of the huTPP1, and was effective in extending the length of time that the enzyme activity was present (FIG. 6), and sustained enzyme activity levels were observed.

Figure 7:
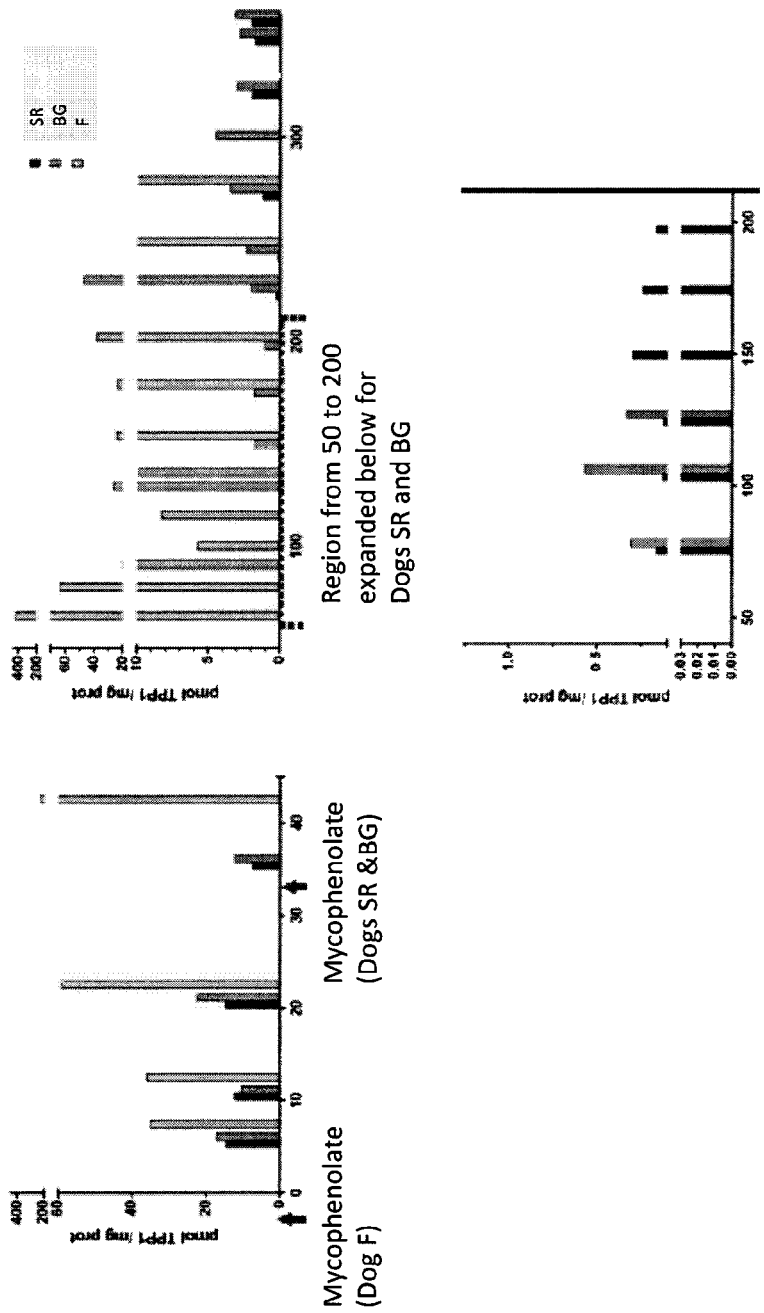
FIG. 7. Introduction of mycophenolate at the time of enzyme activity decline, or prior to gene transfer, dramatically improves the durability of TPP1 expression in dog after AAV.TPP1 delivery to ependyma. Left and right upper graphs: Enzyme activity as a function of time. Also indicated is the time at which mycophenolate was administered. Note the high and sustained levels after recover from loss of expression in Animals SR and B, and the extremely high sustained levels in Animal F. Thus, mycophenolate pretreatment in animals null for recombinant protein helps provide for sustained gene expression in transduced brain cells. Lower graph: Expansion from the upper right graph to demonstrate that there is enzyme over and above background levels, and close to normal levels or above (0.1-0.4 pmol/mg).

High caTPP1 activity in CSF was observed along the time after AAV2caCLN2 intraventricular injection and early mycophenolate treatment (FIG. 7).

Figure 8:
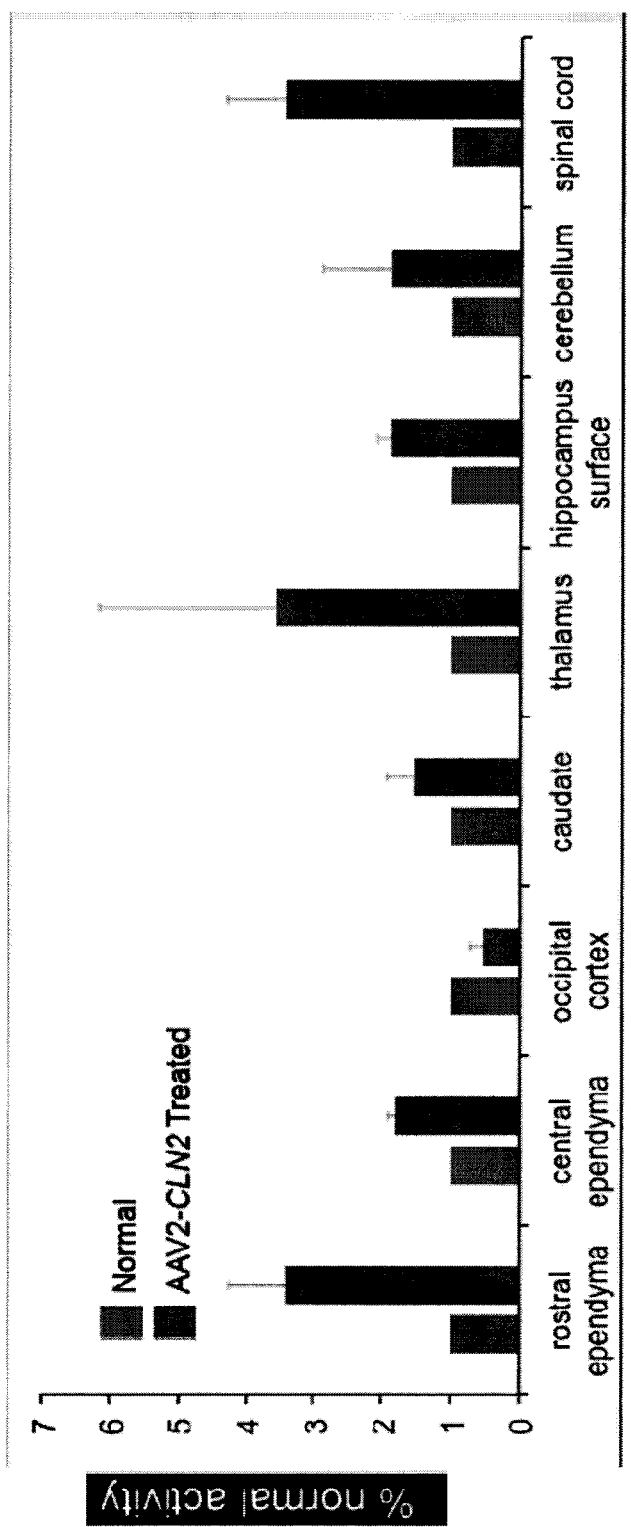
FIG. 8. Sustained enzyme expression in CSF elevates interstitial levels of enzyme. Enzyme activity in various brain regions is above normal.
Figure 9A:
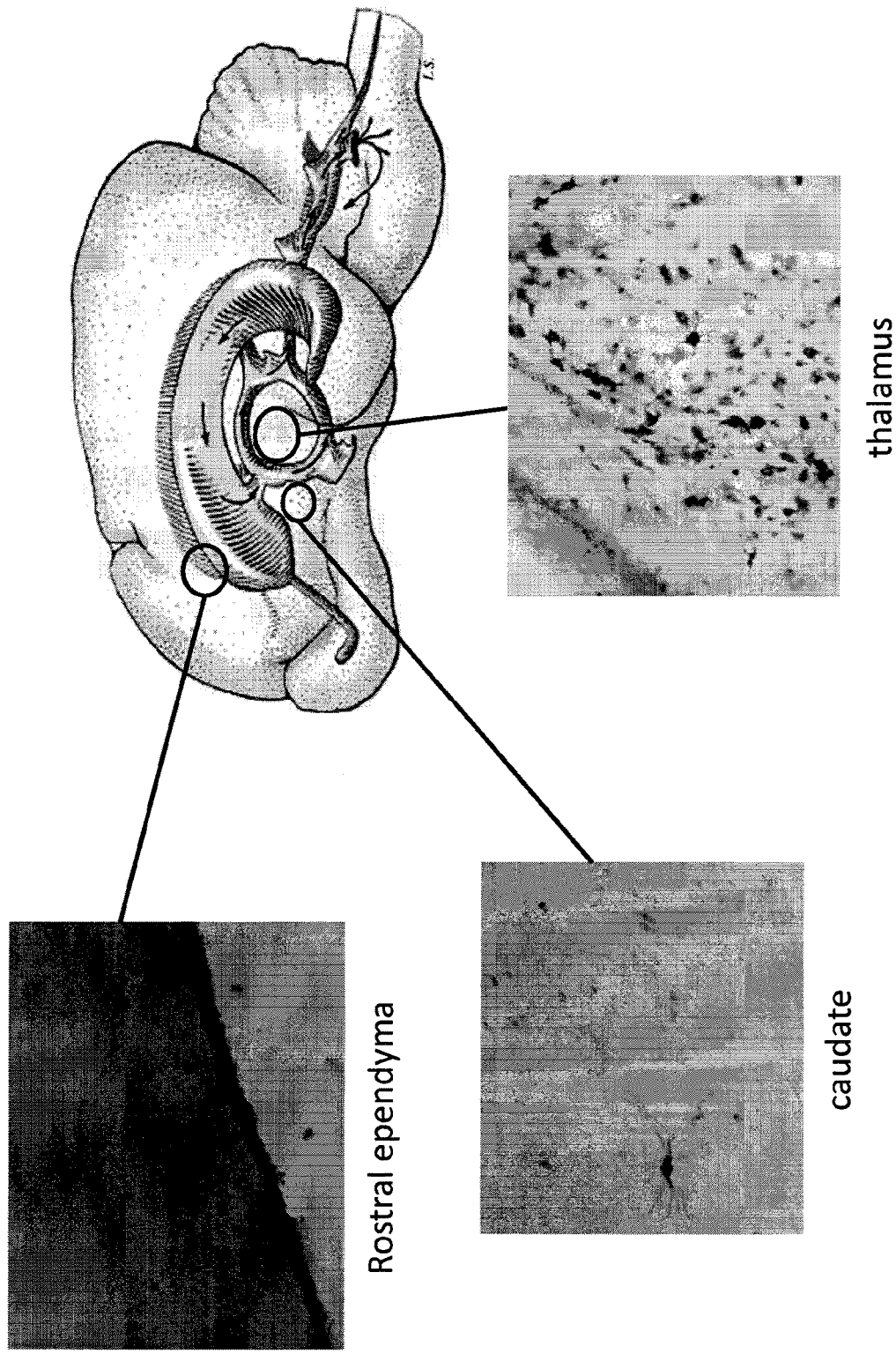
FIGS. 9A and 9B. Immunohistochemical staining in varying brain regions shows extensive distribution of TPP1 protein after AAV.TPP1 gene transfer to the ventricular system of the LINCL dog. Representative panels from the dog brain atlas show the region of the brain being evaluated, which is also depicted by the line. Together the data show extensive distribution of enzyme.
Figure 9B:
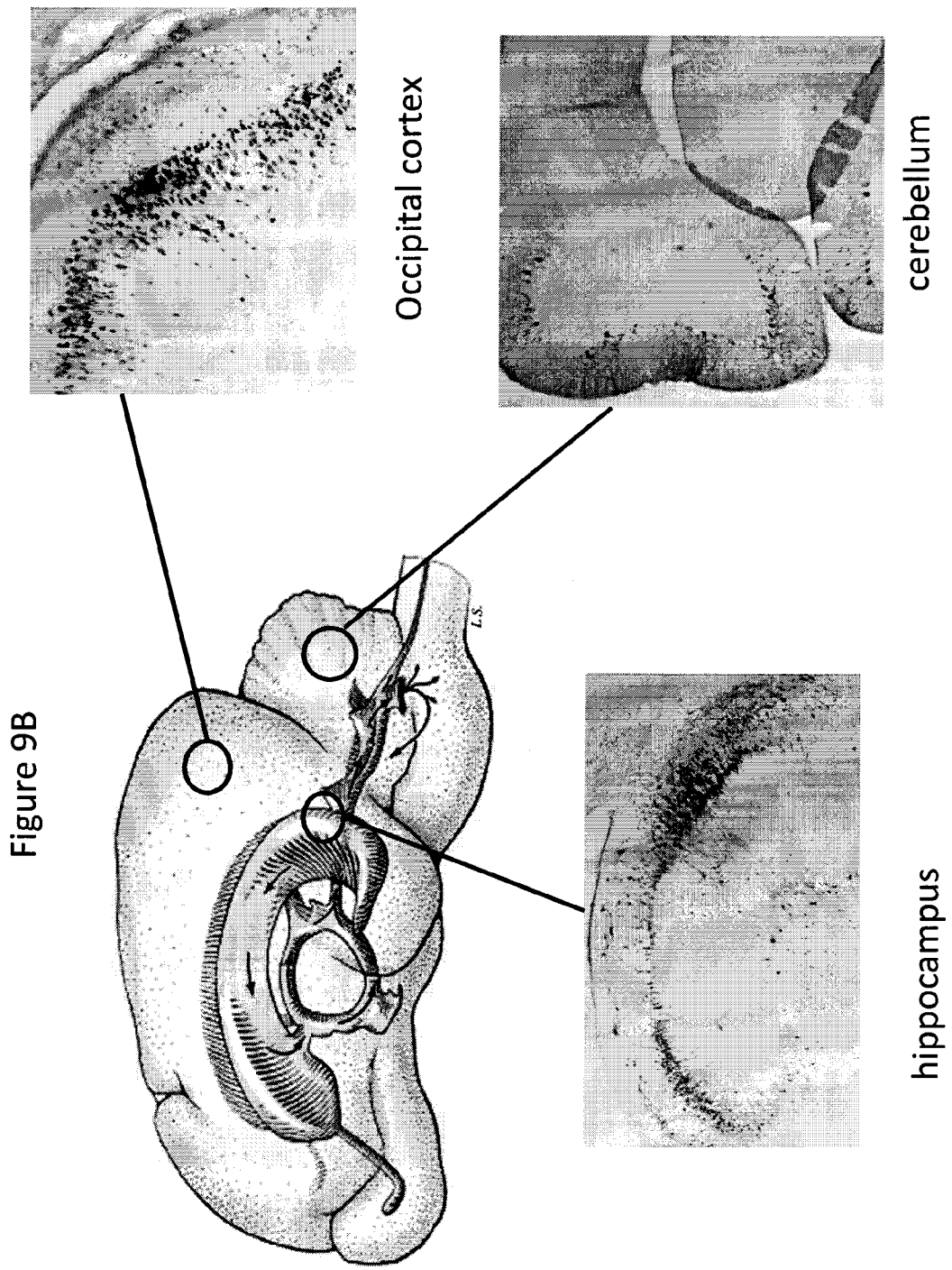

An increase in TPP1 enzyme activity was observed in many tissues two months post-administration (FIGS. 8, 9A and 9B).

Figure 10:
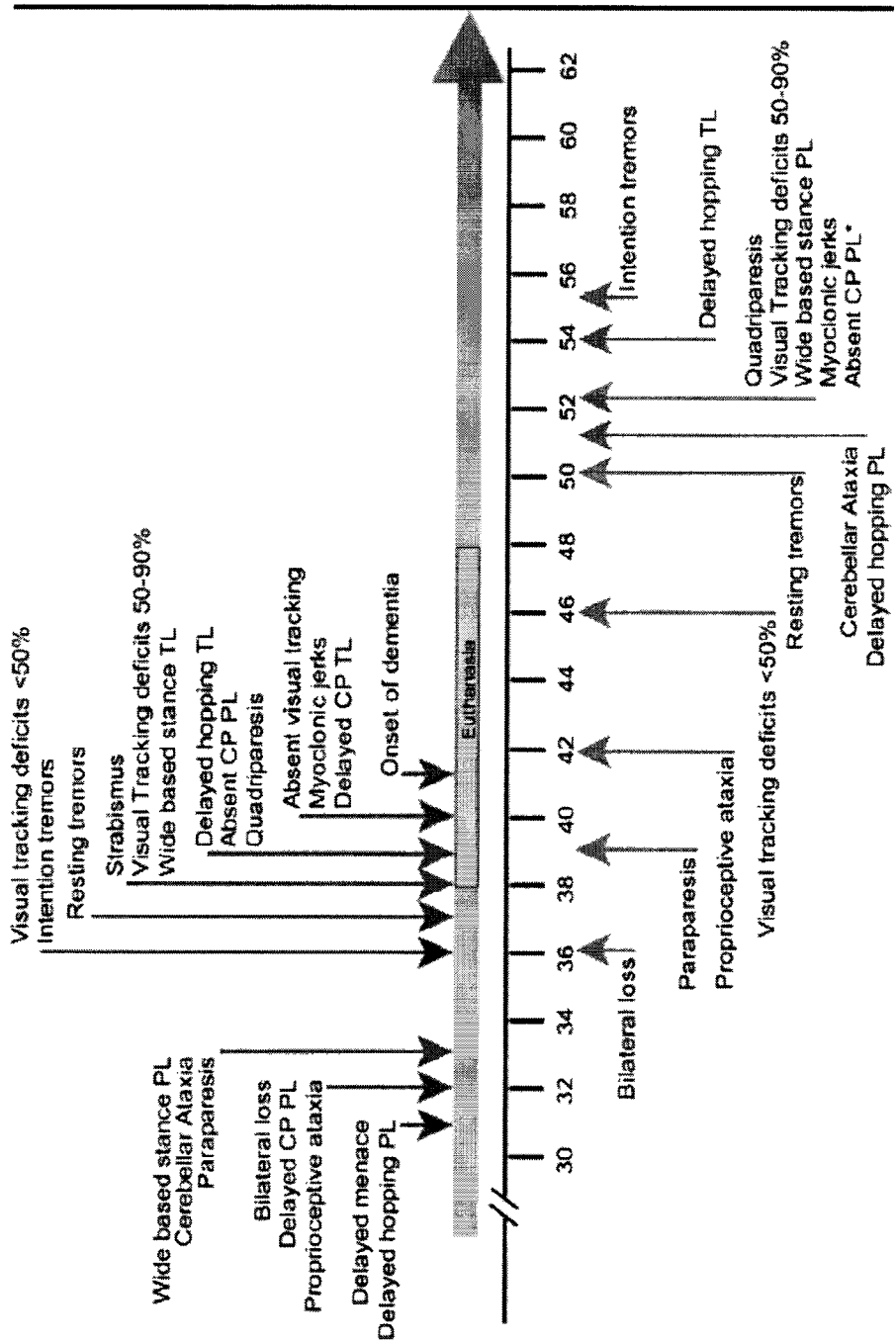
FIG. 10 AAV.TPP1 gene therapy delays the onset of disease phenotypes and the progression of disease. Animal life span was nearly doubled in some dogs, others are still under evaluation.
Figure 11:
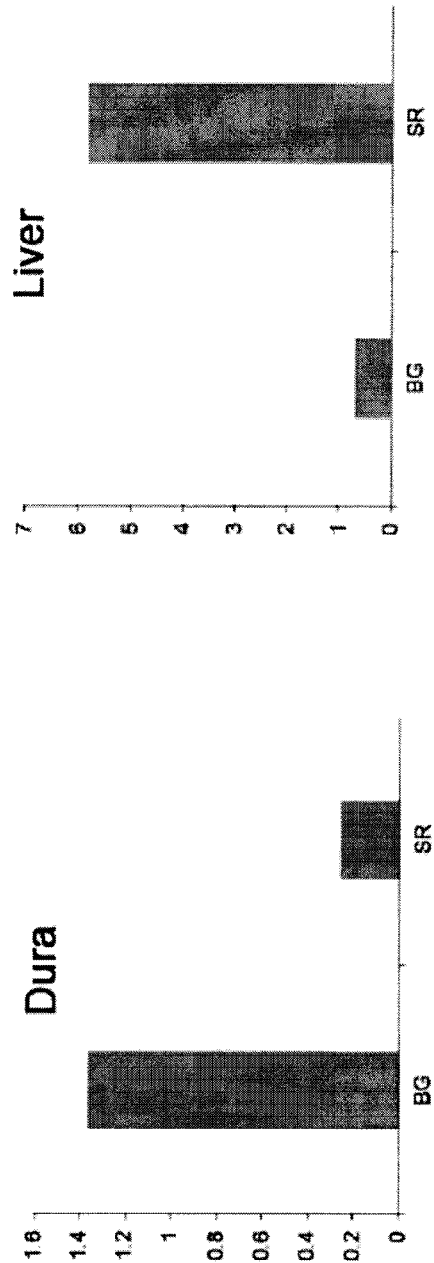
FIG. 11 Animals with sustained TPP1 secretion from ependymal show evidence of enzyme activity in peripheral organs and brain dura. For two animals, BG and SR, there was notable enzyme activity in brain dura and also the liver.

FIG. 10 shows the onset of clinical signs in LINCL dogs. caTPP1 activity was observed in meninges and peripheral tissue, such as the liver (FIG. 11).

Thus, the inventors have shown the transformation of pendymal cells by AAV2/2, that canine TPP1 enzyme was produced and flowed with CSF, and that mycopheolate treatment pro rot caCLN2 injection could prevent immunoresponse in dogs.

Example 2

Studies in Non-Human Primates

Figure 12:
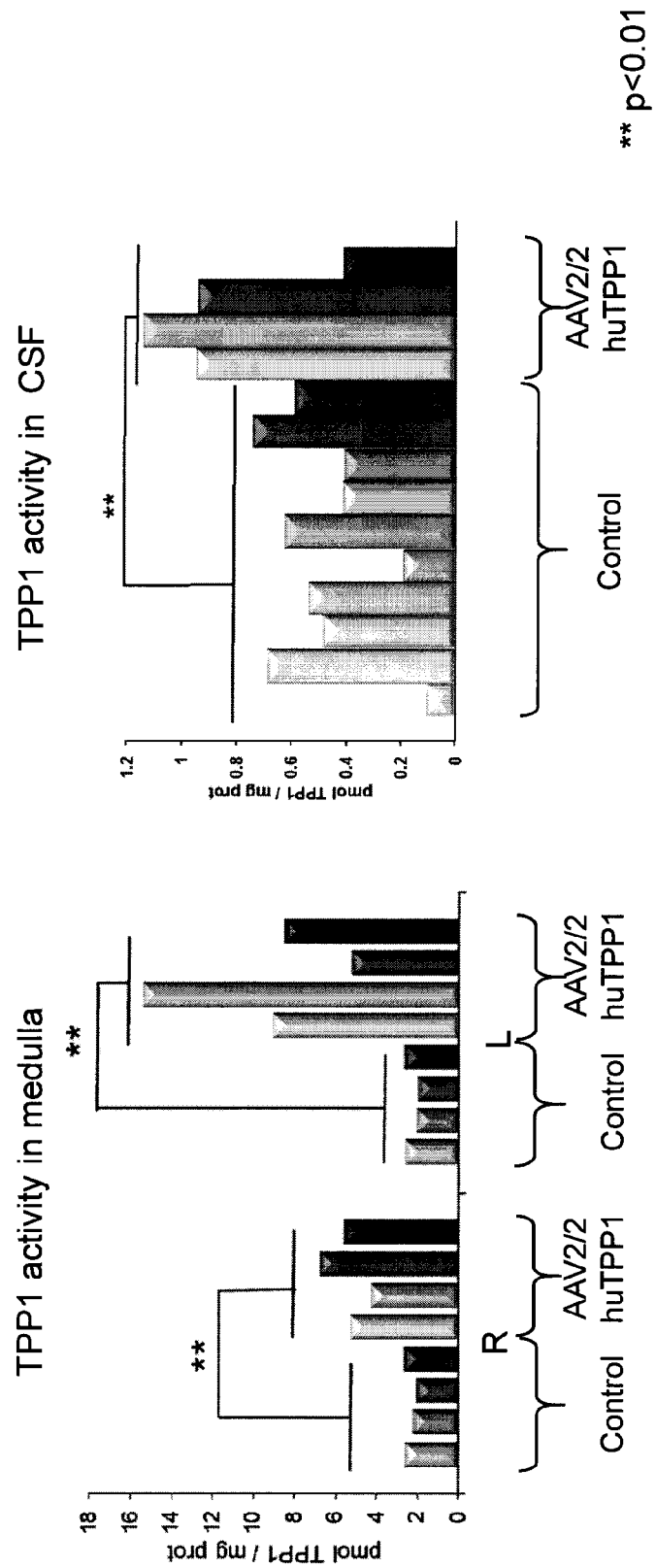
FIG. 12 The approach used to provide clinical benefit to the LINCL dog is translatable to primates. Rhesus macaques were given an intraventricular injection of AAV2.TPP1 (1.5 mL of 1e13 vector genomes/mL) and TPP1 activity in brain stem (Medulla; left graph) and CSF (right graph) measured 3 months after gene transfer. These are normal monkeys with normal levels of TPP1 activity (range noted—Control). In all but one animal, the enzyme activity exceeds that of normal monkeys. Evidence of TPP1 activity in monkey brain 3 months after gene transfer using immunohistochemistry staining against the recombinant human TPP1 expressed from the AAV vector.
Figure 13:
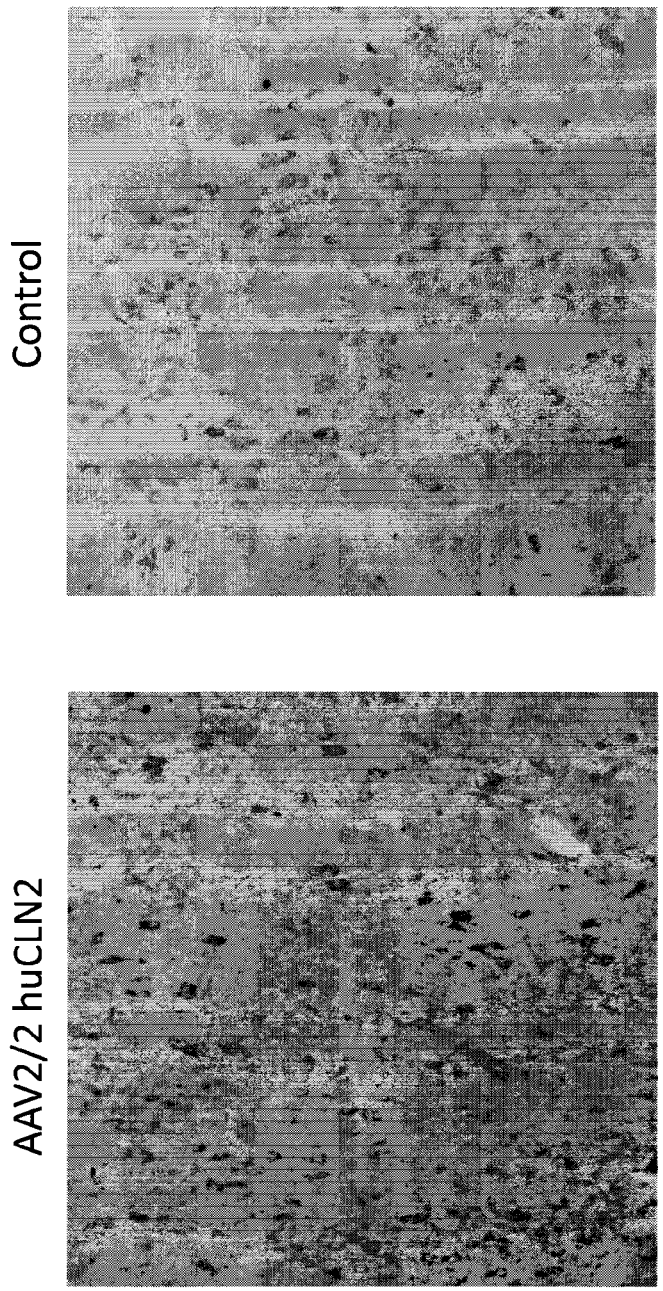
FIG. 13 shows the vestibular area (brainstem) in the non-human primates.

Using techniques similar to those described above, the inventors observed that AAVeGFP transduced ependyma in nonhuman primate brain. In vivo assessment of AAV2/2.TPP1 delivery in rhesus brain was performed by injecting AAV.TPP1 into the ventricle or cisterna magna, harvesting the tissue 4-12 weeks later, and evaluating the TPP1 activity in CSF or tissue lysates (FIG. 12). Activity was observed in the vestibular area (brainstem) in the non-human primates (FIG. 13). Thus, the ventricular lining cells provided a source of recombinant enzyme for broad CNS distribution.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of delivering a therapeutic agent to the central nervous system of a mammal, comprising administering an immunesuppression agent to the mammal and administering to the mammal's cisterna magna, brain ventricle, subarachnoid space, or intrathecal space an rAAV particle comprising an AAV capsid protein and a vector comprising a nucleic acid encoding a therapeutic agent inserted between a pair of AAV inverted terminal repeats in a manner effective to infect a cell that contacts the cerebrospinal fluid (CSF) of the mammal such that the cell expresses the therapeutic agent in the mammal, wherein the therapeutic agent is tripeptidyl peptidase 1 (TPP1), and wherein the mammal is a primate.

2. A method of treating a disease in a mammal comprising administering an immunesuppression agent to the mammal and administering to the mammal's cisterna magna, brain ventricle, subarachnoid space or intrathecal space an rAAV particle comprising an AAV capsid protein and a vector comprising a nucleic acid encoding a therapeutic agent inserted between a pair of AAV inverted terminal repeats in a manner effective to infect a cell that contacts the cerebrospinal fluid (CSF) of the mammal, wherein the cell expresses the therapeutic agent so as to treat the disease, wherein the therapeutic agent is a therapeutic nucleic acid or a protein and wherein the disease is LINCL, wherein the therapeutic agent is TPP1 or CLN2, and wherein the mammal is a primate.

3. The method of claim 1, wherein the cell expresses the therapeutic agent and secretes the therapeutic agent into the CSF.

4. The method of claim 1, wherein the cell is an ependymal, pial, endothelial, brain ventricle, and/or meningeal cell.

5. The method of claim 1, wherein the primate is human.

6. The method of claim 1, wherein the rAAV particle is injected at 1-4 locations in the brain.

7. The method of claim 1, wherein the rAAV particle is an rAAV2, rAAV4, rAAV5 and/or rAAV9 particle.

8. The method of claim 1, wherein the rAAV particle comprising the therapeutic agent is administered in a single dose to the mammal's cisterna magna.

9. The method of claim 1, wherein the immunesuppression agent is an anti-inflammatory agent.

10. The method of claim 9, wherein the anti-inflammatory agent is mycophenolate.

11. The method of claim 1, wherein the immunesuppression agent is administered prior to or with the rAAV particle.

12. The method of claim 2, wherein the cell expresses the therapeutic agent and secretes the therapeutic agent into the CSF.

13. The method of claim 2, wherein the cell is an ependymal, pial, endothelial, brain ventricle, and/or meningeal cell.

14. The method of claim 2, wherein the primate is human.

15. The method of claim 2, wherein the rAAV particle is injected at 1-4 locations in the brain.

16. The method of claim 2, wherein the rAAV particle is an rAAV2, rAAV4, rAAV5 and/or rAAV9 particle.

17. The method of claim 2, wherein the rAAV particle comprising the therapeutic agent is administered in a single dose to the mammal's cisterna magna.

18. The method of claim 2, wherein the immunesuppression agent is an anti-inflammatory agent.

19. The method of claim 18, wherein the anti-inflammatory agent is mycophenolate.

20. The method of claim 2, wherein the immunesuppression agent is administered prior to or with the rAAV particle.

* * * * *